(12) United States Patent
Kang et al.

(10) Patent No.: US 11,718,834 B2
(45) Date of Patent: Aug. 8, 2023

(54) COMPOSITIONS AND METHODS FOR PRODUCING RECOMBINANT AAV

(71) Applicant: Sangamo Therapeutics, Inc., Richmond, CA (US)

(72) Inventors: Andrea J. Kang, Richmond, CA (US); Richard T. Surosky, Richmond, CA (US); Alex Michael Ward, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 666 days.

(21) Appl. No.: 16/790,841

(22) Filed: Feb. 14, 2020

(65) Prior Publication Data

US 2020/0283739 A1    Sep. 10, 2020

Related U.S. Application Data

(60) Provisional application No. 62/806,317, filed on Feb. 15, 2019.

(51) Int. Cl.
*C12N 15/86* (2006.01)
*C12N 15/864* (2006.01)
*A61K 35/761* (2015.01)
*C12N 7/00* (2006.01)

(52) U.S. Cl.
CPC .............. *C12N 7/00* (2013.01); *A61K 35/761* (2013.01); *C12N 15/86* (2013.01); *C12N 15/864* (2013.01); *C12N 2750/14122* (2013.01); *C12N 2750/14132* (2013.01); *C12N 2750/14143* (2013.01)

(58) Field of Classification Search
CPC .......... C12N 15/86; C12N 2750/14162; C12N 15/8645; C12N 15/00; C12N 15/09; C12N 2750/14311; C12N 2750/14143; C12N 15/64; A61K 35/761
See application file for complete search history.

(56) References Cited

U.S. PATENT DOCUMENTS

| | | | |
|---|---|---|---|
| 8,632,765 | B2 | 1/2014 | Samulski |
| 9,506,052 | B2 | 11/2016 | Samulski |
| 9,856,539 | B2 | 1/2018 | Schaffer et al. |
| 10,494,612 | B2 * | 12/2019 | Schaffer .............. A61K 9/0048 |
| 2002/0045264 | A1 | 4/2002 | During et al. |
| 2005/0112765 | A1 | 5/2005 | Li et al. |
| 2006/0166363 | A1 | 7/2006 | Zolotukhin et al. |
| 2006/0188483 | A1 | 8/2006 | Rabinowitz et al. |
| 2007/0238684 | A1 | 10/2007 | Hallek et al. |
| 2008/0050343 | A1 | 2/2008 | Wilson et al. |
| 2012/0093772 | A1 | 4/2012 | Horsager et al. |
| 2014/0099284 | A1 | 4/2014 | Horsager et al. |
| 2014/0359799 | A1 | 12/2014 | Wang et al. |
| 2015/0225741 | A1 | 8/2015 | Horsager et al. |
| 2018/0057839 | A1 | 3/2018 | Willenbring et al. |
| 2018/0230440 | A1 | 8/2018 | Ho et al. |

FOREIGN PATENT DOCUMENTS

| | | |
|---|---|---|
| EP | 1088075 | 9/2006 |
| EP | 2037892 | 3/2015 |
| WO | 2002/000924 | 1/2002 |
| WO | 2005/072364 | 8/2005 |
| WO | 2007/046703 | 4/2007 |
| WO | 2007/148971 | 12/2007 |
| WO | 2008/024998 | 2/2008 |
| WO | 2009/104964 | 8/2009 |
| WO | 2010/099960 | 9/2010 |
| WO | 2013/014294 | 1/2013 |
| WO | 2013/036118 | 3/2013 |
| WO | 2015/054653 A2 | 4/2015 |
| WO | 2017/058892 | 4/2017 |
| WO | 2017/066764 | 4/2017 |
| WO | 2017/161273 | 9/2017 |
| WO | 2017/197355 | 11/2017 |
| WO | 2017/201121 | 11/2017 |
| WO | 2018/002783 A1 | 1/2018 |
| WO | 2018/035441 | 2/2018 |
| WO | 2018/035451 | 2/2018 |
| WO | 2018/035457 | 2/2018 |
| WO | 2018/139634 | 8/2018 |
| WO | 2018/160582 | 9/2018 |

OTHER PUBLICATIONS

Gao et al., "Clades of adeno-associated viruses are widely disseminated in human tissues," Journal of Virology (2004) 78(12):6381-88.
Kearse et al., "Non-AUG translation: a new start for protein synthesis in eukaryotes," Genes Dev. (2017) 31(17):1717-31.
Kondratov et al., "Direct head-to-head evaluation of recombinant adeno-associated viral vectors manufactured in human versus insect cells," Mol Ther. (2017) 25(12):2661-75.
Lobanov et al., "Dual functions of codons in the genetic code," Crit Rev Biochem Mol Biol. (2010) 45(4):257-65.
Maurer et al., "Residues on AAV capsid lumen dictate interactions and compatibility with the assembly-activating protein." Journal of Virology (2019) doi:10.1128/JVI.02013-18.
Maurer et al., "The assembly-activating protein promotes stability and interactions between AAV's viral proteins to nucleate capsid assembly," Cell Reports (2018) 23:1817-30.
Mitchell et al., "AAV's anatomy: roadmap for optimizing vectors for translational success," Curr Gene Ther. (2010) 10(5):319-40.
Popa-Wagner et al., "Impact of VP1-specific protein sequence motifs on adeno-associated virus type 2 intracellular trafficking and nuclear entry," Journal of Virology (2012) 86(17):9163-74.

(Continued)

*Primary Examiner* — Bao Q Li
(74) *Attorney, Agent, or Firm* — Steptoe & Johnson LLP; Z. Ying Li; Debashree Chatterjee

(57) ABSTRACT

Provided herein are nucleic acid constructs, host insect cells, and methods for producing recombinant AAV capsids with high potency at high yield.

16 Claims, 14 Drawing Sheets

Specification includes a Sequence Listing.

(56) References Cited

OTHER PUBLICATIONS

Shen et al., "Characterization of the relationship of AAV capsid domain swapping to liver transduction efficiency," The American Society of Gene Therapy (2007) 15(11):1955-62.
Sonntag et al., "The assembly-activating protein promotes capsid assembly of different adeno-associated virus serotypes," Journal of Virology (2011) 85(23):12686-97.
Venkatakrishnan et al., "Structure and dynamics of adeno-associated virus serotype 1 VP1- unique n-terminal domain and its role in capsid trafficking," Journal of Virology (2013) 87(9):4974-84.
Vercauteren et al., "Superior in vivo transduction of human hepatocytes using engineered AAV3 capsid," The American Society of Gene & Cell Therapy (2016) 24(6):1042-49.
Grosse, et al., "Relevance of assembly-activating protein for adeno-associated virus vector production and capsid protein stability in mammalian and insect cells," Journal of Virology (2017) 91(20):e01198 17.
Bosma et al., "Optimization of viral protein ratios for production of rAAV Serotype 5 in the Baculovirus System," Gene Ther. (2018) 25(6):415-24.
Galibert et al., "Origins of truncated supplementary capsid proteins in rAAV8 vectors produced with the baculovirus system," Plos One (2018).
Girod et al., "The VP1 capsid protein of adeno-associated virus type 2 is carrying a phospholipase A2 domain required for virus infectivity," (2002) Journal of General Virology 83:973-78.
Kohlbrenner et al., "Successful production of pseudotyped rAAV vectors using a modified baculovirus expression system," Mol Ther. (2005) 12(6):1217-25.
Kronenberg et al., "A conformational change in the adeno-associated virus Type 2 capsid leads to the exposure of hidden VP1 N Termini," JVI (2005) 79(9) 5296-303.
Takeuchi et al., "Recombination and population mosaic of a multifunctional viral gene, adeno-associated virus cap," PLoS One (2008) 3(2).
Vliet et al., "Proteolytic mapping of the adeno-associated virus capsid," Mol Ther. (2006) 14(6):809-21.
Aslanidi et al., "An inducible system for highly efficient production of recombinant adeno-associated virus (rAAV) vectors in insect Sf9 cells," Proc Natl Acad Sci USA (2009) 106(13):5059-64.
Balaji et al., "Pseudotyped adeno-associated viral vectors for gene transfer in dermal fibroblasts: implications for wound healing applications," J Surg Res. (2013) 184(1):691-8.
Chen, "Intron splicing-mediated expression of AAV rep and cap genes and production of AAV vectors in insect cells," Mol Ther. (2008) 16(5):924-30.
Clement, et al. "Manufacturing of recombinant adeno-associated viral vectors for clinical trials," Mol Ther Methods Clin Dev. (2016) 3:16002.
Hauck et al., "Generation and Characterization of Chimeric Recombinant AAV Vectors," Mol Ther. (2003) 7(3):419-25.
Jambhekar, "Cis-acting determinants of asymmetric, cytoplasmic RNA transport," RNA (2007) 13(5):625-42.
Li et al., "An intron with a constitutive transport element is retained in a Tap messenger RNA," Nature (2006) 443(7108):234-37.
Mietzsch et al., "OneBac 2.0: Sf9 cell lines for production of AAV1, AAV2, and AAV8 vectors with minimal encapsidation of foreign DNA," Hum Gene Ther Methods (2017) 28(1):15-22.
Rutledge et al., "Infectious clones and vectors derived from adeno-associated virus (AAV) serotypes other than AAV type 2," J Viral. (1998) 72(1):309-19.
Samulski et al., "Helper-free stocks of recombinant adeno-associated viruses: normal integration does not require viral gene expression," J Virol. (1989) 63(9):3822-28.
Smith et al., "A simplified baculovirus-AAV expression vector system coupled with one-step affinity purification yields high-titer rAAV stocks from insect cells," Mol Ther. (2009) 17(11):1888-96.
Urabe et al., "Insect cells as a factory to produce adeno-associated virus type 2 vectors," Hum Gene Ther. (2002) 13:1935-43.
Urabe et al., Scalable generation of high-titer recombinant adeno-associated virus Type 5 in insect cells, J Vir. (2006) 80(4):1874-85.
Zadori et al., "A viral phospholipase A2 is required for parvovirus infectivity," Developmental Cell (2001) 1:291-302.
Zufferey et al., "Woodchuck hepatitis virus posttranscriptional regulatory element enhances expression of transgenes delivered by retroviral vectors," J Virol. (1999) 73(4):2886-92.
Cecchini et al., "Reproducible high yields of recombinant adeno-associated virus produced using invertebrate cells in 0.02- to 200-liter cultures," Hum Gene Ther. (2011) 22:1021-30.
Choi et al., "AAV hybrid serotypes: improved vectors for gene delivery," Curr Gene Ther. (2005) 5(3):299-310.
Earley et al., "Adeno-associated virus (AAV) assembly-activating protein is not an essential requirement for capsid assembly of AAV serotypes 4, 5, and 11," Journal of Virology (2017) 91(3):e01980-16.
Kimczak, et al. "A Novel Adeno-Associated Viral Variant for Efficient and Selective Intravitreal Transduction of Rat Muller Cells," PLoS One (2009) 4(10):e7467.

\* cited by examiner

| Serotype | 158 | 160 | 163 | 165 | 169 | 171 | 173 | 175 | 176 | 177 | 178 | 179 | 180 | 181 | 182 |
|---|---|---|---|---|---|---|---|---|---|---|---|---|---|---|---|
| 1 | S158 T/A | I160 T/V | T163 A/S/K | Q165 K/A | K169R | | | | | | | | S180 A/T | | |
| 4 | T158S /A | I160 T/V | K163 A/S | K165 Q/A | K169R | K171R | V173N | E175G | D176 Q/E | E177T | T178G | G179 D/E | A180 S/T | G181 D/E | D182S |
| 6 | S158 T/A | I160T /V | T163 A/S/K | Q165 K/A | K169R | | | | | | | | S180 A/T | | |
| 7 | T158 S/A | I160T /V | K163 A/S | Q165 K/A | R169K | | | | | | | | S180 A/T | | |
| 8 | T158 S/A | I160T /V | K163 A/S | Q165 K/A | R169K | | | | | | | | S180 A/T | | |
| 11 | S158 T/A | I160T /V | K163 A/S | K165 Q/A | R169K | | | E175G | E176Q | D177T | T178G | G179 D/E | A180 S/T | G181 D/E | D182S |

| Serotype | 183 | 189 | 191 | 192 | 193 | 194 | 195 | 196 | 197 | 198 | 199 | 200 | 201 | 202 | 203 |
|---|---|---|---|---|---|---|---|---|---|---|---|---|---|---|---|
| 1 | | L189 E/I | | | | | T195A | | A197 S/T | A198S/G | V199L | | P201T/S | T202 N/L | |
| 4 | G183V | E189 L/I | S191 Q/E | T192P | S193P | G194A | | M196P | S197T | | | D200G | D201T /S | S202 N/L | E203T |
| 6 | | L189 E/I | | | | | T195A | | A197 S/T | A198S/G | V199L | | P201T/S | T202N /L | |
| 7 | | L189 E/I | | | | | | | S197T | S198G | V199L | | | G202 N/L | |
| 8 | | L189 E/I | | | | | | | S197T | G198S | V199L | | P201T/S | N202L | |
| 11 | G183V | E189 L/I | S191 Q/E | D192P | T193P | S194A | | M196P | S197T | | | S200G | D201 T/S | I202 N/L | E203T |

FIG. 1C

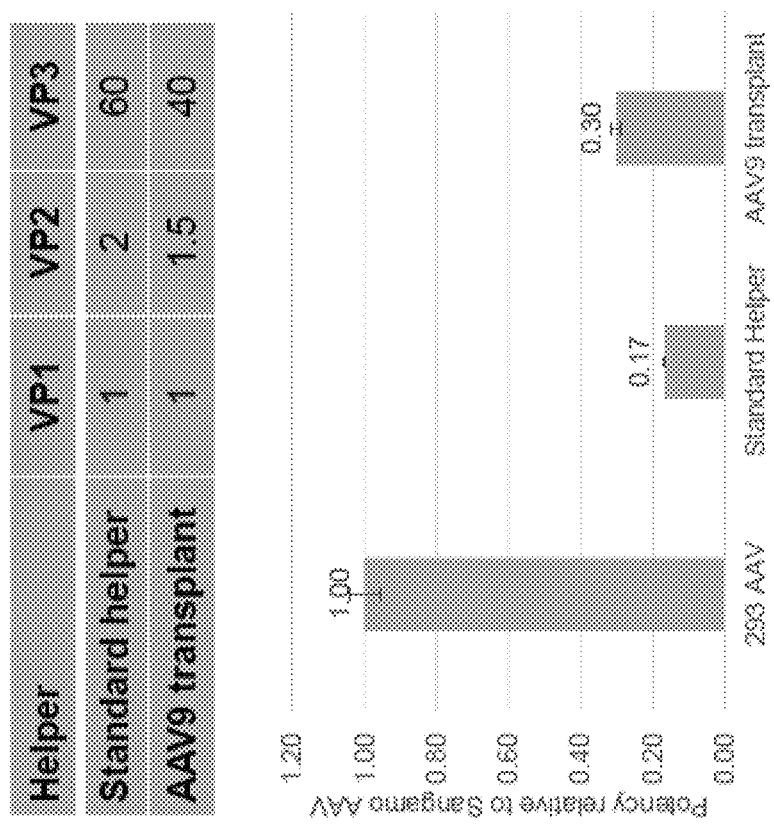
FIG 2B
FIG 2C
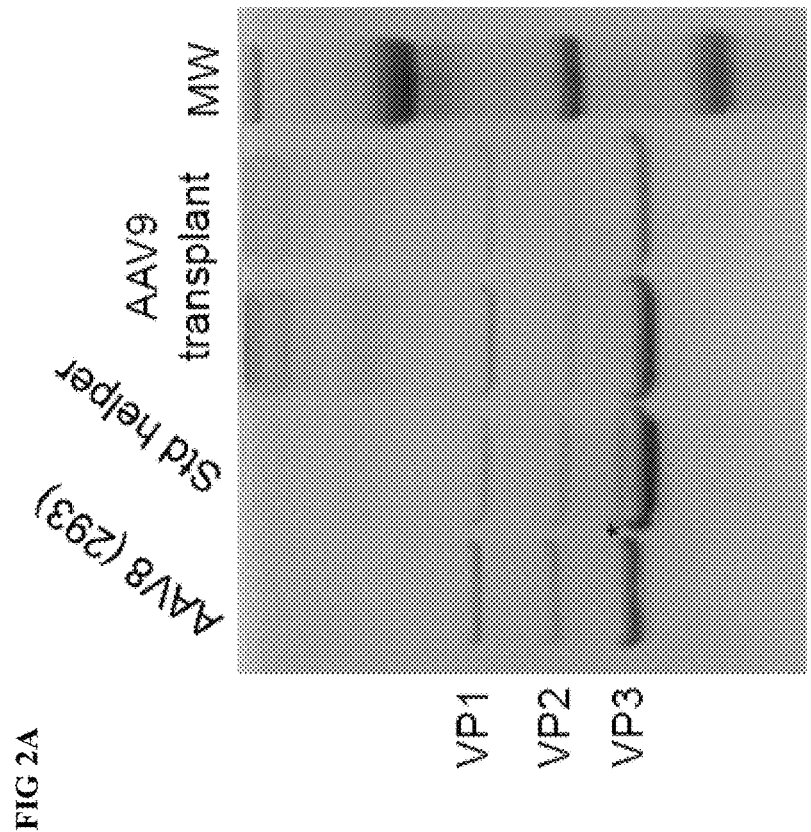
FIG 2A

FIG. 4D

| Serotype | \multicolumn{13}{c|}{Position} |
|---|---|---|---|---|---|---|---|---|---|---|---|---|---|
| | 2 | 3 | 4 | 5 | 6 | 7 | 8 | 9 | 10 | 11 | 12 | 13 | 14 |
| 1 | | | | | | | | | | | | | |
| 2 | E2A | | | T5S | | | P8Q | I9T | H10L | S11N | L12Q | R13S | D14E |
| 4 | E2A | Q3T | A4Q | T5S | D6Q | Y7S | L8Q | | P10L | | L12Q | | D14E |
| 6 | | | | | | P7S | | | | | L12Q | | |
| 7 | | | | | | | P8Q | | H10L | | L12Q | | |
| 8 | | | | | | | P8Q | | | | L12Q | | |
| 10 | | S3T | | | | F7S | | | | | L12Q | | |
| 11 | E2A | P3T | E4Q | T5S | D6Q | P7S | P8Q | | | | Q12L | R13S | D14E |

| Serotype | \multicolumn{14}{c|}{Position} |
|---|---|---|---|---|---|---|---|---|---|---|---|---|---|---|
| | 15 | 16 | 17 | 18 | 19 | 21 | 22 | 23 | 24 | 25 | 26 | 27 | 28 |
| 1 | | L16H | Q17P | | | L21Q | L22V | | | | L26I | | |
| 2 | S15N | H16L | Q17P | E18Q | | L21Q | | L23W | E24D | | I26L | R27Q | |
| 4 | Q15N | L16H | P17Q | | R19P | | C22V | | M24D | T25L | V26I/L | R27Q | C28W |
| 6 | | L16H | Q17P | | R19P | L21Q | L22V | | | | L26I | | |
| 7 | | L16H | Q17P | | R19P | L21Q | | | | | V26I/L | | |
| 8 | | L16H | Q17P | | A19P | L21Q | | | | | I26L | | |
| 10 | | L16H | Q17P | A18Q | | L21Q | | L23W | Q24D | T25L | V26I/L | | |
| 11 | Q15N | I16L/H | P17Q | | | | C22V | | | | L26I | K27Q | C28W |

FIG. 7B

COMPOSITIONS AND METHODS FOR PRODUCING RECOMBINANT AAV

CROSS-REFERENCE TO RELATED APPLICATION

This application claims priority from U.S. Provisional Application 62/806,317, filed Feb. 15, 2019, the content of which is incorporated herein by reference in its entirety.

SEQUENCE LISTING

The instant application contains a Sequence Listing that has been submitted electronically in ASCII format and is hereby incorporated by reference in its entirety. Said ASCII copy, created on Feb. 13, 2020, is named 025297 US004 SL.txt and is 45,255 bytes in size.

BACKGROUND OF THE INVENTION

Adeno-associated virus (AAV) is a small non-enveloped virus belonging to the family Parvoviridae and the genus Dependoparvovirus. AAV is composed of a single-stranded DNA genome packaged into capsids assembled from three capsid proteins—viral protein (VP) 1, VP2, and VP3—at an approximate molar ratio of 1:1:10 (Kondratov et al., Mol Ther. 25(12):2661-75 (2017)). The capsid proteins are encoded by a single capsid (cap) gene and are generated by alternative splicing and differential codon usage (id.). VP1 is the largest capsid protein (81.6 kD). VP2 (66.6 kD) is an N-terminal truncated form of VP1. VP3 (59.9 kD) is an N-terminal truncated form of VP2. See, e.g., Cecchini et al., Hum Gene Ther. 22:1021-30 (2011).

Recombinant AAV (rAAV) has been intensively explored as a vector for gene therapy and DNA vaccines in humans. For rAAV production in mammalian cells, a helper virus (e.g., adenovirus, vaccinia, or herpesvirus) is needed. Over the years, several modifications have been made to facilitate the production of rAAV, including (1) identifying and cloning the minimal set of helper proteins (adenovirus E1, E2A, E4, and VA), (2) providing the AAV Rep (Rep78, Rep68, Rep52, and Rep40) and capsid proteins in trans, and (3) developing a transgene system that allows packaging of DNA sequences flanked by the AAV Inverted Terminal Repeats (ITRs) (Samulski et al., J Virol. 63(9):3822-8 (1989)). When these three components are introduced into mammalian cells, rAAV containing a transgene of interest can be readily purified. Recombinant AAV so produced has been used in clinical trials (Clement and Grieger, Mol Ther Methods Clin Dev. 3:16002 (2016)).

The need for scaled-up rAAV production for larger clinical trials and commercialization has led to the development of insect cell-based production systems that utilize baculoviral vectors to express the Rep and capsid proteins and to carry the coding sequence for a transgene-containing AAV vector genome, which is packaged into rAAV capsids. Such systems do not require adenovirus helper functions (see, e.g., Urabe et al., Hum Gene Ther. 13:1935-43 (2002); Urabe et al., J Vir. 80(4):1874-85 (2006); Chen et al., Mol Ther. 16(5):924-30 (2008); Smith et al., Mol Ther. 17(11):1888-96 (2009); and Mietzsch et al., Hum Gene Ther Methods 28(1):15-22 (2017)). While the baculovirus-insect cell system has been successfully utilized for rAAV production at multiple scales, it has been observed that rAAV generated in insect cells has reduced VP1 content (e.g., with a VP1:VP2: VP3 ratio of approximately 1:1:30 to 1:1:60) and consequently reduced potency, as compared to rAAV produced in mammalian cells (see, e.g., Urabe et al., 2002, supra; Kohlbrenner et al., Mol Ther. 12(6):1217-25 (2005); Urabe et al., 2006, supra; Aslanidi et al., Proc Natl Acad Sci USA 106(13):5059-64 (2009); Kondratov et al., supra; and Mietzsch et al., supra).

Thus, there remains a need for an improved baculovirus-insect cell system for producing rAAV at industrial scales.

SUMMARY OF THE INVENTION

The present disclosure describes modifications made to the AAV cap gene in the baculoviral helper construct that improve the capsid protein ratio, potency, and yield of rAAV produced in a baculovirus-insect cell system.

In one aspect, the present disclosure provides a nucleic acid construct comprising a nucleotide sequence encoding AAV VP1, VP2, and VP3 proteins, wherein the VP1 protein and the VP2 protein comprise two or more mutations at residues 157, 162, 164, 179, 188, 194, 196, 197, 200, and 201 (numbering according to SEQ ID NO:1) relative to wildtype VP1 and VP2 proteins, respectively. As used herein, "numbering according to SEQ ID NO:1" means amino acid residue positions in SEQ ID NO:1, or the corresponding amino acid residue positions in a different VP1 sequence (e.g., VP1 sequence from a serotype other than AAV6). In some embodiments, the VP1 protein and the VP2 protein comprise two or more mutations selected from the group consisting of S157A, T162S, Q164A, S179T, L188I, T194A, A196S, A197G, P200S, and T201L (numbering according to SEQ ID NO:1). In further embodiments, the VP1 protein and the VP2 protein comprise all of these ten mutations.

In some embodiments, the VP1 protein further comprises one or more mutations at residues 67, 81, 84, 85, and 92 relative to wildtype VP1 protein (numbering according to SEQ ID NO:1). In certain embodiments, the VP1 protein comprises one or more mutations selected from the group consisting of A67E, Q81R, K84D, A85S, and R92K. In further embodiments, the VP1 protein comprises all of these five mutations.

In some embodiments, the VP1 protein and the VP2 protein disclosed herein are identical to the VP1 protein and the VP2 protein, respectively, of AAV6 but for the mutations. In particular embodiments, the VP1 protein and the VP2 protein are derived from AAV6 and comprise mutations S157A, T162S, Q164A, S179T, L188I, T194A, A196S, A197G, P200S, and T201L relative to wildtype AAV6 VP1 and VP2 proteins, respectively.

In some embodiments of the nucleic acid construct, the nucleotide sequence also comprises an open reading frame coding for assembly-activating protein (AAP), wherein the AAP comprises one or more mutations at residues 8, 10, 12, 17, 21, and 22 (numbering according to SEQ ID NO:10) relative to wildtype AAP protein. As used herein, "numbering according to SEQ ID NO:10" means amino acid residue positions in SEQ ID NO:10, or the corresponding amino acid residue positions in a different AAP sequence (e.g., AAP sequence from a serotype other than AAV6). In certain embodiments, the AAP comprises one or more (e.g., all) mutations selected from the group consisting of P8Q, H10L, L12Q, Q17P, L21Q, and L22V. In particular embodiments, the AAP is identical to wildtype AAP of AAV6 but for the AAP mutations.

In particular embodiments, the nucleic acid construct of the present disclosure comprises a coding sequence for SEQ ID NO:7, with or without the first amino acid. In further embodiments, the nucleic acid construct comprises nucleotides 18-151 of SEQ ID NO:14. In further embodiments, the nucleic acid construct comprises 10 or more (e.g., 20 or more, 30 or more, 40 or more, 50 or more, 75 or more, 100 or more, 125 or more, or 150 or more) contiguous nucleotides, or the entire nucleotide sequence, of SEQ ID NO:14.

In one aspect, the present disclosure provides a nucleic acid construct comprising a nucleotide sequence encoding AAV VP1, VP2, and VP3 proteins, wherein the VP1 protein comprises one or more mutations at residues 81, 84, 85, and 92 relative to wildtype VP1 protein (numbering according to SEQ ID NO:1). In some embodiments, the VP1 protein comprises one or more mutations selected from the group consisting of Q81R, K84D, A85S, and R92K. In further embodiments, the VP1 protein comprises all of these four mutations. In particular embodiments, the VP1 protein further comprises a mutation at residue 67, e.g., an A67E mutation. In some embodiments, the VP1 protein is identical to the VP1 protein of AAV6 but for the mutation(s). In certain embodiments, the VP1 protein comprises mutations A67E, Q81R, K84D, A85S, and R92K relative to wildtype AAV6 VP1.

In one aspect, the present disclosure provides a nucleic acid construct comprising a nucleotide sequence encoding AAP, wherein the AAP comprises one or more mutations at residues 8, 10, 12, 17, 21, and 22 (numbering according to SEQ ID NO:10) relative to wildtype AAP protein. In some embodiments, the AAP comprises one or more (e.g., all) mutations selected from the group consisting of P8Q, H10L, L12Q, Q17P, L21Q, and L22V.

In some embodiments, the nucleic acid construct of the present disclosure further comprises an AAV rep gene.

In some embodiments, the nucleic acid construct of the present disclosure is a baculoviral vector, wherein the capsid nucleotide sequence is operably linked to a promoter that is active in insect cells.

The present disclosure also provides an insect cell comprising a presently described nucleic acid construct and a recombinant AAV virion produced in the insect cell.

The present disclosure also provides a recombinant AAV virion comprising (i) a genome having a transgene of interest flanked by a pair of AAV Inverted Terminal Repeats (ITR), and (ii) a capsid assembled from the VP1, or both VP1 and VP2 proteins, expressed from a presently described nucleic acid construct.

In yet another aspect, the present disclosure provides a method of producing a recombinant AAV virion, comprising: providing the insect cell described herein, wherein the insect cell also expresses AAV Rep proteins and comprises the coding sequence for an AAV vector comprising a transgene of interest flanked by a pair of AAV ITRs; culturing the insect cell under conditions to allow expression of the VP1, VP2, VP3 proteins, replication of the AAV vector, and packaging of the AAV vector into a capsid assembled from the expressed VP1, VP2, and VP3 proteins, and recovering the packaged capsid. In some embodiments, the gene(s) encoding the AAV Rep, VP1, VP2 and VP3 proteins reside on one or more nucleic acid constructs. In some embodiments, the gene(s) encoding the AAV Rep proteins reside on one or more nucleic acid constructs that are not the nucleic acid construct(s) expressing the VP1, VP2, and VP3 proteins. In some embodiments, the gene(s) encoding the AAV VP1, VP2 and VP3 proteins reside on one or more nucleic acid constructs that are not the nucleic acid construct(s) expressing the Rep proteins. In some embodiments, the gene(s) encoding the Rep proteins and the gene(s) encoding the VP1, VP2, and VP3 proteins are incorporated into the genome of the insect cell.

Also provided in the present disclosure are pharmaceutical compositions comprising the present rAAV and a pharmaceutically acceptable carrier.

Other features, objectives, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

BRIEF DESCRIPTION OF THE FIGURES

FIG. 1C is a table comparing corresponding amino acid positions from AAV serotypes 1, 4, 6, 7, 8, and 11 between amino acid residues 158-203 as aligned in FIG. 1B. The table indicates amino acid mutations that may prevent proteolytic cleavage in these serotypes. Amino acid residue numbers are based on the consensus sequence shown in FIG. 1B.

FIGS. 2A-D show that the substitution of a 45-amino acid stretch of an AAV9 VP1/VP2 (SEQ ID NO:4) for the corresponding region in the AAV6 VP1/VP2 sequence (SEQ ID NO:3) abolishes proteolytic cleavage of the resultant chimeric VP1/VP2 proteins ("AAV6/9 VP1/VP2"). FIG. 2A: Coomassie-stained SDS-PAGE gel analysis of purified rAAV6. Asterisk indicates proteolytic cleavage fragment. FIG. 2B: densitometry and capsid ratio analysis of Standard helper and AAV9 Transplant. FIG. 2C: potency comparison of rAAV6 produced in HEK293 cells ("293 AAV") or in Sf9 cells ("Standard Helper" and "AAV9 transplant"). FIG. 2D: alignment of the transplanted AAV9 cap nucleotide sequence and the AAV6 cap nucleotide sequence that was replaced in AAV9 Transplant; the arrow "A" indicates the AAP start codon. The AAV6 contained a Factor IX ("FIX") transgene, and the virus's potency was assayed by viral transduction of HepG2 cells and subsequent measurement of FIX expression in the cells with ELISA. Potency was calculated relative to rAAV6 produced in HEK293 cells ("293 AAV"). Standard (Std) helper: baculoviral helper vector whose AAV6 cap gene does not contain a heterologous sequence from another serotype. AAV9 Transplant: baculoviral helper vector whose AAV6 cap gene contains a sequence from the AAV9 cap gene, as described above and further below. FIG. 2D discloses SEQ ID NOs:13 and 14, respectively, in order of appearance.

FIGS. 4A-D illustrate that variants of AAV6/9 VP1/VP2 prevented cleavage, but did not improve potency of the AAV capsid. FIG. 4A: a sequence alignment of Variants 1, 2, 3, and 4 of AAV6/9 VP1/VP2 (numbering according to SEQ ID NO:1). FIG. 4A discloses SEQ ID NOs:32-37, respectively, in order of appearance. FIG. 4B: a photograph of a Coomassie-stained SDS-PAGE gel. *: proteolytic cleavage product. **: additional cleavage product. FIG. 4C: a bar graph showing relative potency of various AAV products. Ref: 293 AAV. Other definitions are the same as above. FIG. 4D: partial alignment of the cap/AAP nucleotide sequences and the AAP amino acid sequences (in rectangle) of AAV6, AAV9 Transplant, Variant 1, Variant 2, Variant 3, and Variant 4. The AAP amino acid sequence of AAV9 Transplant has six mutations (P8Q, H10L, L12Q, Q17P, L21Q, and L22V) relative to that of AAP6 in the indicated region, while the AAP amino acid sequences of Variants 1-3 each have only two mutations (L21Q and L22V). Variant 4 has the native AAP6 sequence in the indicated region. FIG. 4D discloses SEQ ID NOs:38-44, 43, 45, 43 and 46-47, respectively, in order of appearance.

FIG. 5A: capsid protein ratios of VP1:VP2:VP3 as determined SDS-PAGE and Coomassie Blue densitometry. FIG. 5B: potency comparison of rAAV6 produced in (i) 293 cells or (ii) Sf9 insect cells containing the Standard helper or the AAV6 helper providing an engineered AAV6 VP1 with the AAV2 PLA2 domain. Potency was determined by using FIX cDNA transduction and ELISA for detection of FIX expression, and was calculated relative to 293 AAV.

FIG. 7B shows the amino acid differences in the indicated AAP region (consensus numbering) between (i) AAV1, AAV2, AAV4, AAV6, AAV7, AAV8, AAV10, or AAV11 and (ii) AAV9 or AAV3B. Amino acid residue numbers are based on the consensus sequence shown in FIG. 7A.

DETAILED DESCRIPTION OF THE INVENTION

Figure 1A:
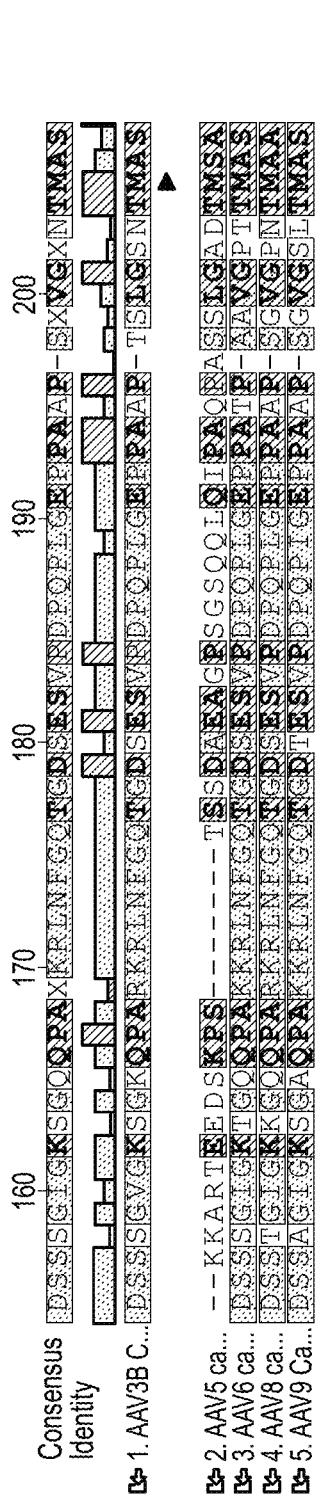
FIG. 1A shows the alignment of the VP1/VP2 amino acid sequences (SEQ ID NOs:16-21, respectively, in order of appearance) from AAV serotypes 3B, 5, 6, 8, and 9 between amino acid residues 155 and 207 (numbering based on consensus sequence). N-terminal Edman degradation sequencing was performed on the proteolytic cleavage products cored from an SDS-PAGE gel to identify the proteolytic cleavage site in AAV6 VP1/VP2. The cleavage site maps to residues $G_{190}E_{191}$. Multiple sequence alignment was generated using the Geneious software package and default settings for ClustalW alignment. The VP3 start site is indicated by the triangle at residue 205.

The present disclosure provides improved baculovirus-insect cell systems and related compositions for producing potent rAAV capsids at high yield. In the systems, the cap gene in the baculoviral helper construct is mutated in two or more codons such that the VP1 and VP2 proteins encoded by the gene are resistant to proteolytic degradation during the production process. Because the cap gene also contains the open reading frame for AAP, these codon changes may also cause mutations in the AAP. The inventors have made the unexpected discovery that the mutations in VP1/VP2 and/or AAP improve the rAAV's infectivity, i.e., potency. Without being bound by theory, the inventors contemplate that the increase in potency may be attributed to the improved integrity of the capsid proteins in insect cells and the improved abilities of the mutated AAP to facilitate capsid assembly.

Additionally or alternatively, the cap gene in the baculoviral helper construct is mutated in one or more codons in the region coding for the VP1 PLA2 domain such that the engineered PLA2 domain acquires higher enzymatic activity. The inventors have made the unexpected discovery that higher PLA2 enzymatic activity may lead to a higher yield of rAAV in the insect cell production system.

As used herein, when a particular AAV serotype is referred to, it refers to the prototype for the serotype as well as various isolates within the same Glade of this prototype. For AAV Glade categorization, see, e.g., Gao et al., *J Viral.* (2004) 78(12):6381-8, the disclosure of which is incorporated herein by reference in its entirety.

Removal of Proteolytic Sites in AAV VP1NP2 Proteins

In some embodiments, the present improved baculovirus-insect cell systems can be used to produce any AAV serotype that is susceptible to proteolysis in insect cells. Such AAV serotypes may include, for example, AAV1, AAV6, AAV8, or variants thereof, or any pseudotyped or chimeric rAAV whose VP1/VP2 proteins are susceptible to proteolysis in insect cells.

By "pseudotyped" or "cross-packaged" rAAV is meant a recombinant AAV whose capsid is replaced with the capsid of another AAV serotype, to, for example, alter transduction efficacy or tropism profiles of the virus (e.g., Balaji et al., *J Surg Res.* 184(1):691-8 (2013)). By "chimeric" or "hybrid" rAAV is meant a recombinant AAV whose capsid is assembled from capsid proteins derived from different serotypes and/or whose capsid proteins are chimeric proteins with sequences derived from different serotypes (e.g., serotypes 1 and 2; see, e.g., Hauck et al., *Mol Ther.* 7(3):419-25 (2003)).

In an improved AAV production system of the present disclosure, two or more point mutations are introduced to AAV VP1/VP2 proteins derived from, e.g., AAV1, AAV4, AAV6, AAV7, AAV8, or AAV11, to remove the sites susceptible to proteolysis in insect cells. The introduced point mutations may be residues identical to those at the corresponding positions in AAV2, AAV3, AAV5, AAV9, or AAV10.

By "corresponding" amino acid residue or region is meant an amino acid residue or region that aligns with (though not necessarily identical to) the reference residue or region, when the subject sequence and the reference sequence containing the residues or regions are aligned to achieve maximum homology (allowing gaps that are recognized in the art). For example, amino acid residue 189 (L) of AAV8 VP1 corresponds to amino acid residue 188 of AAV6 VP1.

In some embodiments, the baculoviral helper construct of the present disclosure provides helper functions for the production of rAAV6, and the helper construct includes a modified AAV6 cap gene (cap6) encoding a mutated VP1 protein. The complete amino acid sequence of an AAV6 VP1 protein is shown below, where the start sites of VP2 (T) and VP3 (M) are boldfaced and underlined:

(SEQ ID NO: 1)

```
  1 XAADGYLPDW LEDNLSEGIR EWWDLKPGAP KPKANQQKQD DGRGLVLPGY KYLGPFNGLD

61 KGEPVNAADA AALEHDKAYD QQLKAGDNPY LRYNHADAEF QERLQEDTSF GGNLGRAVFQ

121 AKKRVLEPFG LVEEGAKTAP GKKRPVEQSP QEPDSSSGIG KTGQQPAKKR LNFGQTGDSE

181 SVPDPQPLGE PPATPAAVGP TTMASGGGAP MADNNEGADG VGNASGNWHC DSTWLGDRVI

241 TTSTRTWALP TYNNHLYKQI SSASTGASND NHYFGYSTPW GYFDFNRFHC HFSPRDWQRL

301 INNNWGFRPK RLNFKLFNIQ VKEVTTNDGV TTIANNLTST VQVFSDSEYQ LPYVLGSAHQ

361 GCLPPFPADV FMIPQYGYLT LNNGSQAVGR SSFYCLEYFP SQMLRTGNNF TFSYTFEDVP

421 FHSSYAHSQS LDRLMNPLID QYLYYLNRTQ NQSGSAQNKD LLFSRGSPAG MSVQPKNWLP

481 GPCYRQQRVS KTKTDNNNSN FTWTGASKYN LNGRESIINP GTAMASHKDD KDKFFPMSGV

541 MIFGKESAGA SNTALDNVMI TDEEEIKATN PVATERFGTV AVNLQSSSTD PATGDVHVMG

601 ALPGMVWQDR DVYLQGPIWA KIPHTDGHFH PSPLMGGFGL KHPPPQILIK NTPVPANPPA

661 EFSATKFASF ITQYSTGQVS VEIEWELQKE NSKRWNPEVQ YTSNYAKSAN VDFTVDNNGL

721 YTEPRPIGTR YLTRPL
```

In the sequence above, X in position 1 may be M (wildtype; source: GenBank AAB95450.1), T, L, or V. In other embodiments, the VP1 start residue may be another amino acid encoded by a non-canonical start codon such as a suboptimal start codon. See, e.g., Kearse et al., *Genes Dev.* 31:1717-31 (2017).

In some embodiments, the above AAV6 VP1/VP2 proteins comprise mutations relative to the wildtype at two or more residues in a region corresponding to residues 138-203 (e.g., residues 151-201 or residues 157-201) of SEQ ID NO:1, where the mutated residues are selected from a group consisting of residues 157, 162, 164, 179, 188, 194, 196, 197, 200, and 201. In some embodiments, the AAV6 VP1/VP2 proteins comprise two or more mutations selected from the group consisting of S157A, T162S, Q164A, S179T, L188I, T194A, A196S, A197G, P200S, and T201L (numbering according to SEQ ID NO:1). For example, an AAV6 VP1/VP2 protein may have the mutations (i) S179T, L188I, T194A, A196S, A197G, P200S, and T201L ("Variant 1"); (ii) S179T, L188I, T194A, A196S, and A197G ("Variant 2"); (iii) T194A, A196S, A197G, P200S, and T201L ("Variant 3"); (iv) S157A, T162S, and Q164A ("Variant 4"); or (v) P200S and T201L. For convenience, only the residue numbers in VP1 are referred to herein. The numbers of the corresponding residues in VP2 can be readily discerned from SEQ ID NO:1 above. For example, residue S157 in VP1 is residue S20 in VP2.

In particular embodiments, the AAV6 VP1/VP2 proteins comprise the mutation L188I and one or more other mutations in the group. For example, the AAV6 VP1/VP2 proteins may have the mutations L188I, P200S, and T201L.

In some embodiments, the AAV6 VP1/VP2 proteins comprise all ten mutations of S157A, T162S, Q164A, S179T, L188I, T194A, A196S, A197G, P200S, and T201L, such that their sequence in the region corresponding to residues 157-201 in SEQ ID NO:1 is as follows.
    AGIGKSGAQP    AKKRLNFGQT    GDTESVPDPQ
        PIGEPPAAPS GVGSL (SEQ ID NO:4)
This sequence is identical to the sequence in the corresponding region in AAV9 VP1/VP2.

Thus, to generate a modified cap6 gene in a baculoviral AAV6 helper construct, one can replace the coding sequence for residues 157-201 of VP1 (i.e., residues 20-64 of VP2; SEQ ID NO:3) with the coding sequence for the corresponding amino acid sequence (SEQ ID NO:4) of AAV9, using well known molecular clone techniques; the resultant modified baculoviral AAV6 helper construct is referred to herein as "AAV9 Transplant" and the resultant VP1/VP2 proteins are referred to herein as "AAV6/9 VP1/VP2." In some embodiments, the portion of the AAV6 cap gene sequence that is replaced comprises the underlined sequence shown below (see also FIG. 2D):

(SEQ ID NO: 13)
AAGAGCCAGACTCCTCC<u>TCGGGCATTGGCAAGACAGGCCAGCAGCCCG

CTAAAAAGAGACTCAATTTTGGTCAGACTGGCGACTCAGAGTCAGTCC

CCGACCCACAACCTCTCGGAGAACCTCCAGCAACCCCCGCTGCTGTGG

GACCTAC</u>TACAATGGCTTCAGGCGGTGGCGCACCAATGG

In certain embodiments, the underlined portion in SEQ ID NO: 13 is replaced by a corresponding cap gene sequence from AAV9 to generate an AAV9 Transplant disclosed herein. In particular embodiments, the AAV9 cap sequence transplanted to the AAV6 cap gene in an AAV9 Transplant comprises the underlined sequence shown below (see also FIG. 2D):

(SEQ ID NO: 14)
AAGAGCCAGACTCCTCC<u>GCGGGTATTGGCAAATCGGGTGCACAGCCCG

CTAAAAAGAGACTCAATTTCGGTCAGACTGGCGACACAGAGTCAGTCC

CAGACCCTCAACCAATCGGAGAACCTCCCGCAGCCCCCTCAGGTGTGG

GATCTCTT</u>ACAATGGCTTCAGGCGGTGGCGCACCAATGG

In other embodiments, a modified cap6 gene in the baculoviral AAV6 helper construct can be generated by replacing the coding sequence for residues 157-201 of VP1 in SEQ ID NO:1 (i.e., residues 20-64 of VP2; SEQ ID NO:3) with the coding sequence for the corresponding amino acid sequence from a serotype whose VP1/VP2 proteins are resistant to proteolytic cleavage in insect cells, e.g., AAV2, AAV3, AAV3B, AAV5, or AAV10.

In other embodiments, the VP1/VP2 proteins of AAV serotypes, such as AAV1, AAV4, AAV7, AAV8, or AAV11, can be mutated such that they contain one or more mutations shown in FIG. 1C. The resultant proteins are expected to be more resistant to proteolysis in insect cells. Unlimiting examples of engineered VP1/VP2 proteins from various AAV serotypes are shown below:

(1) the engineered AAV1 VP1/VP2 proteins may contain one or more of the following mutations: S158T/A, I160T/V, T163A/S/K, Q165K/A, K169R, S180A/T, L189E/I, T195A, A197S/T, A198S/G, V199L, P201T/S, and T202N/L;

(2) the engineered AAV4 VP1/VP2 proteins may contain one or more of the following mutations: T158S/A, I160T/V, K163A/S, K165Q/A, K169R, K171R, V173N, E175G, D176Q/E, E177T, T178G, G179D/E, A180S/T, G181D/E, D182S, G183V, E189L/I, S191Q/E, T192P, S193P, G194A, M196P, S197T, D200G, D201T/S, S202N/L, and E203T;

(3) the engineered AAV6 VP1/VP2 proteins may contain one or more of the following mutations: S158T/A, I160T/V, T163A/S/K, Q165K/A, K169R, S180A/T, L189E/I, T195A, A197S/T, A198S/G, V199L, P201T/S, and T202N/L;

(4) the engineered AAV7 VP1/VP2 proteins may contain one or more of the following mutations: T158S/A, I160T/V, K163A/S, Q165K/A, R169K, S180A/T, L189E/I, S197T, S198G, V199L, and G202N/L;

(5) the engineered AAV8 VP1/VP2 proteins may contain one or more of the following mutations: T158S/A, I160T/V, K163A/S, Q165K/A, R169K, S180A/T, L189E/I, S197T, G198S, V199L, P201T/S, and N202L; and (6) the engineered AAV11 VP1/VP2 proteins may contain one or more of the following mutations: S158T/A, I160T/V, K163A/S, K165Q/A, R169K, E175G, E176Q, D177T, T178G, G179D/E, A180S/T, G181D/E, D182S, G183V, E189L/I, S191Q/E, D192P, T193P, S194A, M196P, S197T, S200G, D201T/S, I202N/L, and E203T (consensus numbering; see FIG. 1C).

In some embodiments, the VP1/VP2 proteins from an AAV serotype susceptible to proteolysis in insect cells are mutated to contain one or more mutations at the following amino acid residues (consensus numbering in FIG. 1C): 158, 163, 165, 180, 189, 195, 197, 198, 201, and 202. (These residues correspond respectively to amino acid residues 157, 162, 164, 179, 188, 194, 196, 197, 200, and 201 according to the numbering of SEQ ID NO:1 (AAV6) or a corresponding sequence from another serotype aligned to show maximal homology to SEQ ID NO:1.) In further embodiments, the VP1/VP2 proteins may additionally contain one or more mutations at the following amino acid residues (consensus numbering in FIG. 1C): 160, 169, 171-179, 181-183, 191-194, 196, 199, and 203.

In some embodiments, the VP1/VP2 proteins from an AAV serotype susceptible to proteolysis in insect cells are mutated to contain one or more mutations: S158T/A, I160T/V, K/T163S/A/T, Q165K/A, K169R, K171R, V173N, E175G, D176Q/E, D/E177T, T178G, G179D/E, S180A/T, G181D/E, D182S, G183V, L189E/I, Q/S191E, T/D192P, S/T193P, G/S194A, T/G195A, M196P, A197S/T, A198G/S, V199L, S200G, D/P201S/T, T/S202N/L, and E203T (consensus numbering in FIG. 1C).

In some embodiments, the engineered VP1/VP2 proteins may contain one or more of the following mutations: S158A, T163S, Q165A, 5180T, L189I, T195A, A197S, A198G, P201S, and T202L (consensus number in FIG. 1C). (These residues correspond respectively to amino acid residues S157A, T162S, Q164A, S179T, L188I, T194A, A196S, A197G, P200S, and T201L according to the numbering of SEQ ID NO:1 (AAV6) or a corresponding sequence from another serotype aligned to show maximal homology to SEQ ID NO:1.)

The mutations described herein remove sites in the AAV capsid proteins susceptible to proteolytic cleavage in insect cells. Thus, a helper construct containing the modified cap gene will give rise to rAAV products of higher purity and uniformity, as well as improved capsid protein.

Surprisingly, we have found that the point mutations introduced herein to the AAV VP1/VP2 unique region (i.e., region common to VP1 and VP2 but absent in VP3) can also significantly improve the rAAV's potency through a mechanism that does not rely on solely on the prevention of proteolytic cleavage.

Improvement of rAAV Production Yield

The present disclosure also provides a baculovirus-insect system in which the cap gene in the baculoviral helper construct is altered in the VP1 unique region (i.e., region present in VP1 but not in VP2 or VP3) to improve the production yield of the rAAV in insect cells. The VP1 unique region (corresponding to residues 1-137 of SEQ ID NO:1) contains the PLA2 domain, and the mutations in the region may increase the enzymatic activity of the PLA2 domain in the resultant VP1 protein.

In some embodiments, the baculoviral helper construct of the present disclosure provides helper functions for the production of rAAV6 or rAAV9 and the helper construct includes a modified AAV6 or AAV9 cap gene (cap6 or cap9, respectively) with a mutated PLA2 domain. The mutated PLA2 domain may comprise mutations relative to the wild-type at one or more positions in a region corresponding to residues 1-137 (e.g., 52-97 or 67-92) of SEQ ID NO:1, where the positions are selected from a group consisting of residues 67, 81, 84, 85, and 92 (numbering of SEQ ID NO:1). In some embodiments, the AAV6 VP1 protein comprises one or more mutations selected from the group consisting of A67E, Q81R, K84D, A85S, and R92K (numbering according to SEQ ID NO:1). In particular embodiments, the AAV6 VP1 protein comprises all of the five mutations, such that its sequence in the region corresponding to residues 52-97 (SEQ ID NO:5) in SEQ ID NO:1 is as follows.

YLGPFNGLDK GEPVNEADAA ALEHDKAYDR QLDSGDNPYL KYNHAD (SEQ ID NO:6)

This sequence is identical to the sequence in the corresponding region in AAV2 VP1. Thus, to generate a modified cap6 gene in the baculoviral AAV6 helper construct, one can replace the coding sequence for residues 52-97 or 67-92 of VP1 with the coding sequence for the corresponding amino acid sequence of AAV2, using well known molecular cloning techniques.

Surprisingly, we have found that the point mutations introduced herein to the AAV VP1 unique region can significantly improve the VP1 PLA2 domain's enzymatic activity and also lead to significant improvement (e.g., two or more fold, three or more fold, four or more fold, or five or more fold) in the yield of the rAAV produced in insect cells.

In particular embodiments, the engineered cap gene encodes an AAV6 VP1 protein containing both the aforementioned mutations in the PLA2 domain and the aforementioned mutations that remove the proteolytic sites. One exemplary modified AAV6 VP1 protein ("AAV6/2/9 VP1") has the following sequence:

```
                                                           (SEQ ID NO: 7)
  1 MAADGYLPDW LEDNLSEGIR EWWDLKPGAP KPKANQQKQD DGRGLVLPGY KYLGPFNGLD

61 KGEPVNEADA AALEHDKAYD RQLDSGDNPY LKYNHADAEF QERLQEDTSF GGNLGRAVFQ

121 AKKRVLEPFG LVEEGAKTAP GKKRPVEQSP QEPDSSAGIG KSGAQPAKKR LNFGQTGDTE

181 SVPDPQPIGE PPAAPSGVGS LTMASGGGAP MADNNEGADG VGNASGNWHC DSTWLGDRVI

241 TTSTRTWALP TYNNHLYKQI SSASTGASND NHYFGYSTPW GYFDFNRFHC HFSPRDWQRL

301 INNNWGFRPK RLNFKLFNIQ VKEVTTNDGV TTIANNLTST VQVFSDSEYQ LPYVLGSAHQ

361 GCLPPFPADV FMIPQYGYLT LNNGSQAVGR SSFYCLEYFP SQMLRTGNNF TFSYTFEDVP

421 FHSSYAHSQS LDRLMNPLID QYLYYLNRTQ NQSGSAQNKD LLFSRGSPAG MSVQPKNWLP

481 GPCYRQQRVS KTKTDNNNSN FTWTGASKYN LNGRESIINP GTAMASHKDD KDKFFPMSGV

541 MIFGKESAGA SNTALDNVMI TDEEEIKATN PVATERFGTV AVNLQSSSTD PATGDVHVMG

601 ALPGMVWQDR DVYLQGPIWA KIPHTDGHFH PSPLMGGFGL KHPPPQILIK NTPVPANPPA

661 EFSATKFASF ITQYSTGQVS VEIEWELQKE NSKRWNPEVQ YTSNYAKSAN VDFTVDNNGL

721 YTEPRPIGTR YLTRPL
```

Other exemplary modified AAV6 VP1 protein has the same sequence as SEQ ID NO:7 except that the start residue in position is not present or is T, L, V, or another amino acid encoded by a non-canonical start codon such as a suboptimal start codon. A baculoviral helper construct encoding one of these modified AAV6 VP1 proteins can be used to produce rAAV6 or a pseudotyped or chimeric rAAV with improved potency and yield in insect cells.

Modifications to AAP

In another aspect, the present disclosure provides an AAV helper construct encoding an engineered AAP that has improved abilities to stabilize capsid protein and to facilitate capsid assembly. The inventors have discovered that when residues 1-30 of AAV6 AAP ("AAP6") are changed to residues 1-30 AAV9 AAP ("AAP9"), the potency of the rAAV produced with the engineered helper construct is significantly increased. Residues 1-30 of AAP6 and AAP9 are shown below, where the six amino acid differences in wildtype AAP9 relative to wildtype AAP6 are indicated by boldface and boxes:

```
                                       (SEQ ID NO: 8)
AAV6 AAP:    MATQSQSPTH NLSENLQQPP LLWDLLQWLQ (SEQ ID NO: 9)
AAV9 AAP:    MATQSQSQIL NQSENLPQPP QVWDLLQWLQ
```

The complete AAV6 AAP wild-type sequence is shown below:

```
                                       (SEQ ID NO: 10)
  MATQSQSPTH NLSENLQQPP LLWDLLQWLQ AVAHQWQTIT

KAPTEWVMPQ EIGIAIPHGW ATESSPPAPE HGPCPPITTT

STSKSPVLQR GPATTTTSA TAPPGGILIS TDSTAISHHV

TGSDSSTTIG DSGPRDSTSS SSTSKSRRSR RMMASRPSLI

TLPARFKSSR TRSTSCRTSS ALRTRAASLR SRRTCS
```

Figure 7A:
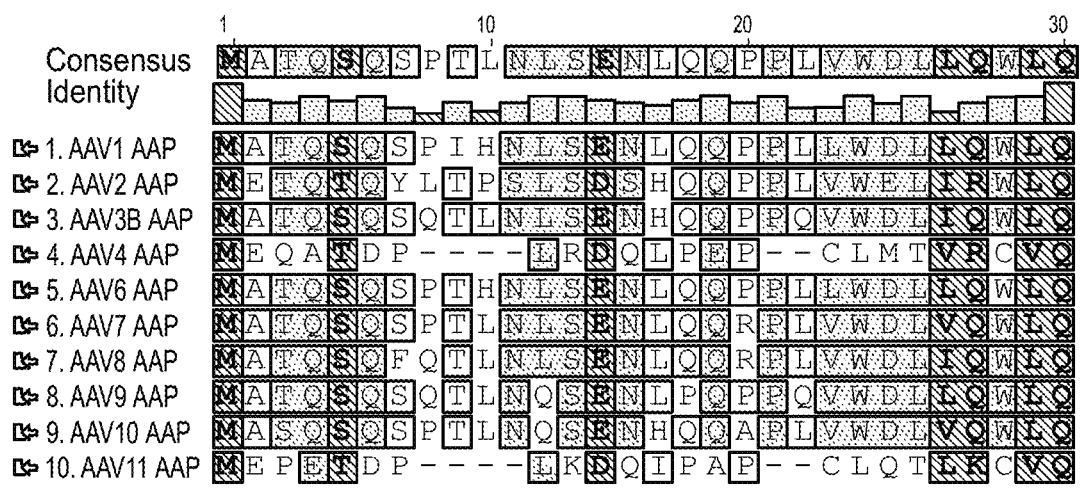
FIG. 7A shows the alignment of the assembly-activating protein (AAP) amino acid sequences (SEQ ID NOs:48-52, 8, 53-54, 9 and 55-56, respectively, in order of appearance) from AAV serotypes 1, 2, 3B, 4, and 6-11 in the indicated region. Amino acid residue numbers are based on the consensus sequence. Multiple sequence alignment was generated using the Geneious software package and default settings for ClustalW alignment.

In some embodiments, the engineered AAP protein comprises one or more mutations at residues 8, 10, 12, 17, 21, and 22 (numbering based on consensus sequence in FIG. 7A). In further embodiments, the engineered AAP protein may comprise one or more of the following amino acid residues: Q8, L10, Q12, P17, Q21, and V22. In some embodiments, the engineered AAP protein may comprise one or more of the following mutations relative to the wildtype AAP sequence: P8Q, H10L, L12Q, Q17P, L21Q, and L22V. Unlimiting examples of engineered, improved AAP proteins are shown below:

(1) engineered AAP1 (AAP of serotype 1) comprising one or more of the following mutations: P8Q, I9T, H10L, L12Q, L16H, Q17P, L21Q, L22V, and L26I;

(2) engineered AAP2 (AAP of serotype 2) comprising one or more of the following mutations: E2A, T5S, Y7S, L8Q, P10L, S11N, L12Q, D14E, S15N, H16L, Q17P, L21Q, E24D, I26L, and R27Q;

(3) engineered AAP4 (AAP of serotype 4) comprising one or more of the following mutations: E2A, Q3T, A4Q, T5S, D6Q, P7S, L12Q, R13S, D14E, Q15N, L16H, P17Q, E18Q, C22V, L23W, M24D, T25L, V26I/L, R27Q, and C28W;

(4) engineered AAP6 (AAP of serotype 6) comprising one or more of the following mutations: P8Q, H10L, L12Q, L16H, Q17P, L21Q, L22V, and L26I;

(5) engineered AAP7 (AAP of serotype 7) comprising one or more of the following mutations: P8Q, L12Q, L16H, Q17P, L21Q, L22V, and L26I;

(6) engineered AAP8 (AAP of serotype 8) comprising one or more of the following mutations: F7S, L12Q, L16H, Q17P, R19P, L21Q, and I26L;

(7) engineered AAP10 (AAP of serotype 10) comprising one or more of the following mutations: S3T, P8Q, Q12L, L16H, Q17P, A19P, L21Q, and V26I/L; and (8) engineered AAP11 (AAP of serotype 11) comprising one or more of the following mutations: E2A, P3T, E4Q, T5S, D6Q, P7S, L12Q, R13S, D14E, Q15N, I16L/H, P17Q, A18Q, C22V, L23W, Q24D, T25L, L26I, K27Q, and C28W (see also FIG. 7B).

To generate engineered AAP protein, one can perform point mutations. Because the open reading frame encoding AAP is embedded in the cap gene and is translated merely by a frameshift, one may also transplant from another serotype a portion of the cap gene containing the coding sequence for an N terminal portion of AAP (e.g., residues 1-30, residues 1-28, residues 2-30, residues 2-28, etc.). In some embodiments, an AAV9 cap gene portion coding for an AAV9 VP1/VP2 unique region (i.e., region common to VP1 and VP2 but absent in VP3), for example, a cap9 sequence comprising nucleotides 18-151 of SEQ ID NO:14 is substituted for the corresponding region of cap6, to generate an engineered baculoviral helper construct expressing an engineered AAV6 VP1/VP2 with a portion of AAV9 VP1/VP2 (e.g., so as to remove the proteolytic site(s) as discussed above), as well as an engineered AAP6 whose N-terminal 1-30 amino acid residues are now identical to those of AAP9. In some embodiments, the AAP mutations are generated by the same method as described above for the AAV9 cap gene transplant and as further described in Example 1 below.

Production of rAAV in Insect Cells

Production of rAAV in insect cells can be performed as described previously. See, e.g., Urabe et al., 2002 and 2006, supra; Chen et al., supra; Smith et al., supra; Mietzsch et al., supra; WO 2007/046703, WO 2007/148971, WO 2009/104964, WO 2013/036118, and WO 2008/024998, all of which are incorporated herein by reference in their entirety.

The insect cells in the production methods of the present disclosure comprise a baculoviral helper construct having an expression cassette encoding a modified cap gene described herein. The insect cells may be, without limitation, a cultured cell line such as BTI-TN-5B1-4 derived from *Trichoplusia ni* (High Five™, ThermoFisher Scientific, Carlsbad, Calif.), 519 cells or Sf21 cells (both of which are derived from *Spodoptera frupperda*), Sf9 or TN368 cells with mammalian-type glycan profiles (GlycoBac), or Sf-RVN cells (MilliporeSigma). The insect cells additionally comprise, on the same helper construct or on an additional helper construct, an expression cassette comprising an AAV rep gene. The helper construct(s) in the insect cells comprise transcription regulatory elements that direct and regulate the expression of the Rep proteins and the capsid proteins. These elements include, without limitation: constitutive or inducible promoters that are active in insect cells (e.g., a p5 promoter, a p10 promoter, a p19 promoter, a p40 promoter, a polh promoter, an E1 promoter, and a ΔE1 promoter); Kozak sequences; transcription initiation and termination sites (either modified or unmodified); mRNA splice sites (either modified or unmodified, within or adjacent to the polypeptide coding sequence; and viral, eukaryotic, or prokaryotic RNA elements that control splicing, nuclear export, localization, stabilization, or translation of mRNAs (e.g., Woodchuck hepatitis virus posttranscriptional regulatory element (WPRE) (Zufferey et al., *J Virol.* 73(4):2886-92 (1999)), MMLV/MPMV, eukaryotic constitutive transport element (CTE) (Li et al., *Nature* 443(7108):234-7 (2006)), RNA zipcodes (Jambhekar and DeRisi, RNA 13(5):625-42 (2007)), and omega or other 5'-UTR RNA elements that increase translational efficiency). The rep and/or cap gene on the helper construct(s) may be codon-optimized, for example, to modulate expression levels of the polypeptide products, to remove potential undesired transcription/translation initiation sites, to remove cryptic promoter activity, and/or to remove destabilizing elements (e.g., Smith et al., supra).

The rAAV may comprise within its capsid an AAV vector containing a transgene of interest. The transgene may encode a reporter protein for detection using biochemical (luciferase, SEAP) or imaging (GFP, Venus, dTomato) techniques. The transgene may encode a therapeutic protein, including, without limitation, a chimeric antigen receptor (CAR), a C-peptide or insulin, collagen VII, IGF-I, lipoprotein lipase, fibrinogen, prothrombin, Factor V, Factor VIII, Factor IX, Factor XI, Factor XII, Factor XIII, von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, and plasminogen activator inhibitor-2. The transgene may encode a sequence-specific nuclease (ZFN, TALEN or Cas9) or sequence-specific binding protein (ZFP, TALE or dCas9). The transgene may carry a sequence that can be incorporated into a specific site in the host genome (donor) by homologous recombination to express a therapeutic protein (as described above). The transgene may encode an immunogenic protein for vaccination (e.g., a tumor antigen).

The AAV vector may comprise transcription regulatory elements (e.g., promoter and enhancer) that can direct and regulate expression of the transgene in human cells. The AAV vector may also comprise an AAV complete or partial inverted terminal repeat (ITR) on one or both ends of the transgene expression cassette. ITRs are required for packaging and viral integration into the host (human) genome.

Pharmaceutical Compositions of rAAV

The rAAV capsids produced by the present methods can be formulated with a pharmaceutically acceptable carrier as a pharmaceutical composition. Formulations include, without limitation, suspensions in liquid or emulsified liquids. Pharmaceutically acceptable carriers include, for example, water, saline, dextrose, glycerol, sucrose, or the like, and combinations thereof. In addition, the composition may contain auxiliary substances, such as, wetting or emulsifying agents, pH buffering agents, stabilizing agents, or other reagents that enhance the effectiveness of the rAAV pharmaceutical composition.

The rAAV pharmaceutical composition may be delivered in vivo by administration to the patient, for example, by systemic administration (e.g., intravenous, intraperitoneal, intramuscular, subdermal, intrathecal, or intracranial infusion) or local injections. Alternatively, the rAAV can be delivered to cells ex vivo, such as cells explanted from a patient (e.g., lymphocytes, bone marrow aspirates, or tissue biopsy) or allogeneic cells (e.g., universal donor cells such as universal CAR T cells), followed by introduction of the treated cells into the patient, usually after selection for cells that have incorporated the rAAV vector.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. In case of conflict, the present specification, including definitions, will control. Generally, nomenclature used in connection with, and techniques of, cell and tissue culture, molecular biology, virology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art.

In order that this invention may be better understood, the following examples are set forth. These examples are for purposes of illustration only and are not to be construed as limiting the scope of the invention in any manner.

EXAMPLES

For the following Working Examples, AAV with a transgene comprising a Factor IX (FIX) expression cassette was produced in HEK293 (mammalian) cells using the triple transfection method, or in Sf9 (insect) cells by infecting naïve Sf9 cells with baculovirus-infected insect cells (BIICs) expressing either Rep/Cap protein or providing the AAV genome; the produced AAV was purified using discontinuous cesium chloride density gradients (reviewed in Clement and Grieger, supra). Following purification, AAV samples were analyzed by Taqman qPCR using transgene-specific primer probes to quantify viral particle (vg) content. AAV samples (~2×10$^{11}$ vg total) were combined with loading dye and reducing agent, incubated at 95° C. for 5 min, loaded on 4-12% NuPAGE™ gels (ThermoFisher Scientific) and electrophoresed for 80 min at 150 V. Gels were stained with SimplyBlue SafeStain (ThermoFisher Scientific) and destained according to the manufacturer's instructions. Destained gels were scanned using the Li-Cor Odyssey CLx (Li-Cor Biosciences), and bands were quantitated using the Li-Cor Odyssey software. Capsid ratios were calculated relative to VP1 and normalized to the protein molecular weight. To test the potency of AAV, HepG2 cells were transduced with an MOI (multiplicity of infection) of 1×10$^6$ vg/cell and incubated for 5 days. After 5 days, tissue culture supernatant was collected and FIX protein expression was quantitated using a FIX ELISA kit (Affinity Biologicals, Inc). FIX content in each sample was quantitated based on the standard curve and calculated as relative potency compared to 293 AAV (AAV produced in HEK293 cells).

Example 1: Elimination of Proteolytic Cleavage Sites in rAAV6

We produced several AAV serotypes in the insect cell system as described above and found that an extra protein fragment was co-purified on cesium chloride density gradient with the expected VP1, VP2, and VP3 proteins for serotypes 6 and 8. This extra protein fragment was seen as an extra band slightly above the VP3 band in Coomassie Blue-stained SDS-PAGE gel, indicating that it was a proteolytic cleavage product of VP1/VP2. This cleavage product was not observed for serotype 3B (Rutledge et al., J Virol. 72(1):309-19 (1998)), 5, or 9 produced in insect cells. This cleavage product also was not observed for serotype 6 produced in HEK293 cells. These data suggest that the VP1/VP2 proteins of certain AAV serotypes, e.g., serotypes 6 and 8, are susceptible to proteolytic cleavage in insect cells.

Figure 1B:
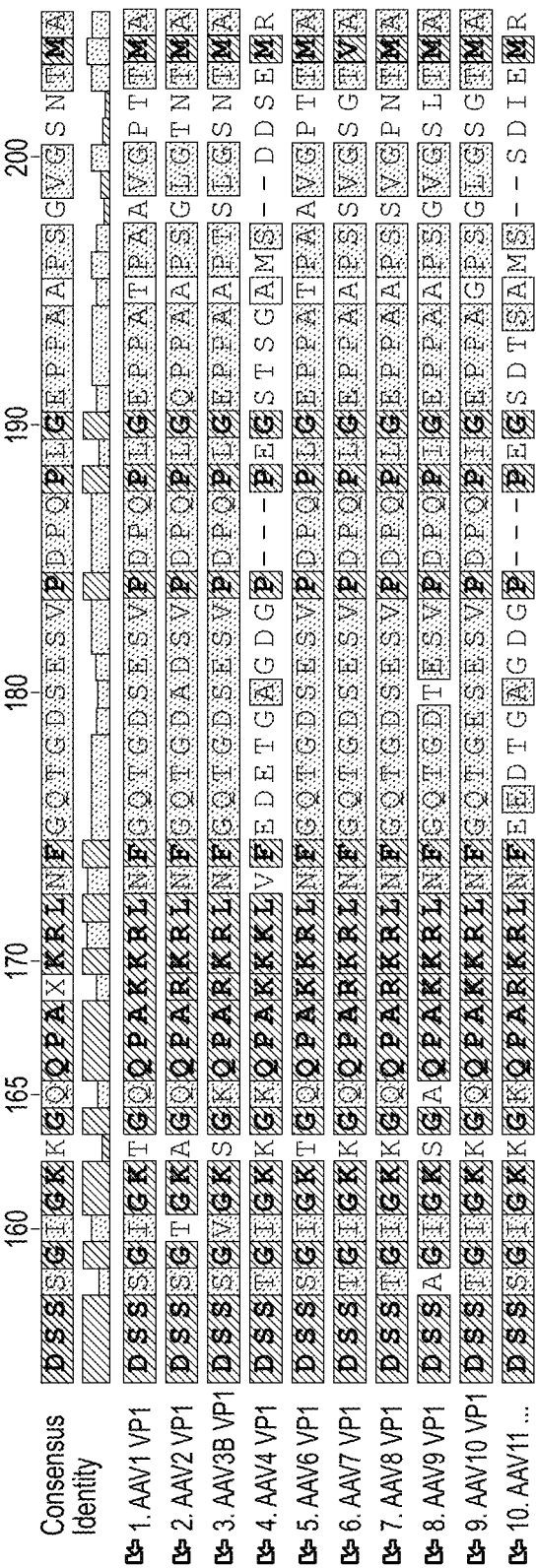
FIG. 1B shows the alignment of the VP1/VP2 amino acid sequences (SEQ ID NOs:22-26, 23, and 27-31, respectively, in order of appearance) from AAV serotypes 1, 2, 3B, 4, and 6-11 between amino acid residues 155 and 205 (numbering based on consensus sequence). Multiple sequence alignment was generated using the Geneious software package and default settings for ClustalW alignment.

We performed Edman degradation sequencing on the extra protein fragment from AAV6 and determined that its N-terminal sequence was EPPAT (SEQ ID NO:15), consistent with a proteolytic cleavage site in the sequence PQPLG↓EPPAT (SEQ ID NO:2; "↓" denotes the cleavage point). Sequence alignment of the VP1/VP2 leader sequences of multiple AAV serotypes just before the start of the VP3 protein revealed that this sequence in AAV6 was divergent from serotypes 3B, 5, 8 and 9 (FIGS. 1A and 1B).

Figure 2D:
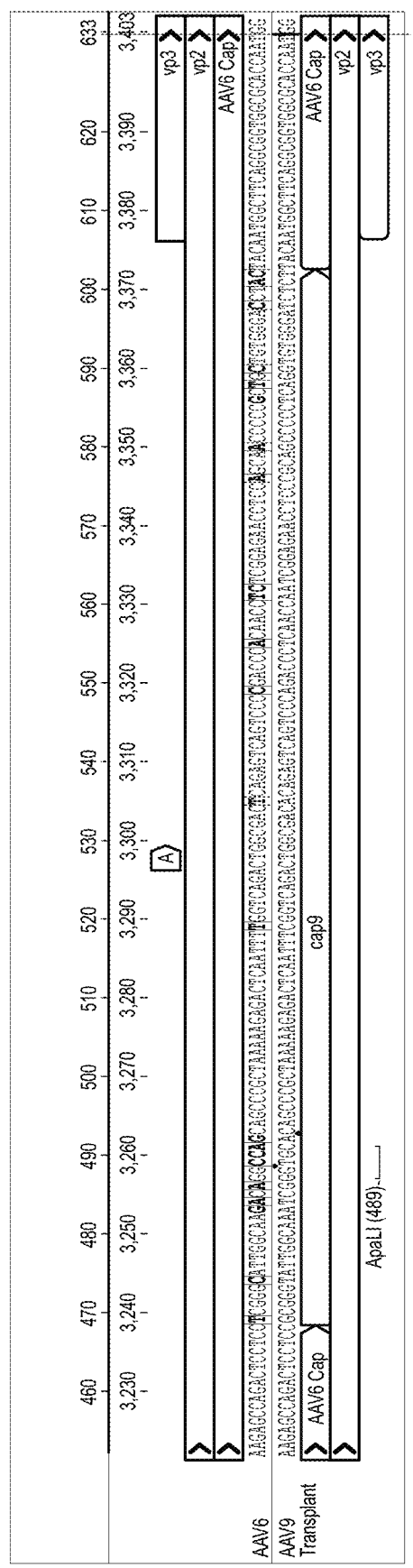

To test whether the proteolytic cleavage could be prevented by altering the sequence around the AAV6 cleavage site, we transferred the nucleotide sequence from AAV9 corresponding to 45 amino acids prior to the VP3 start codon into the AAV6 cap (cap6) gene in the baculo-helper vector for AAV6 (FIG. 2D). The wildtype AAV6 and AAV9 sequences in this region (residues 157-201 of SEQ ID NO:1) are shown below, where the amino acid changes relative to wildtype AAV6 after the AAV9 sequence transplant are boldfaced and boxed:

```
                                            (SEQ ID NO: 3)
AAV6    SGIGKTGQQP AKKRLNFGQT GDSESVPDPQ PLGEPPATPA

AVGPT (SEQ ID NO: 4)
AAV9    AGIGKSGAQP AKKRLNFGQT GDTESVPDPQ PLGEPPAAPS

GVGSI
```

This transfer resulted in ten amino acid changes in total in the resultant AAV6 VP1/VP2 unique region. When rAAV6 was produced using a baculovirus helper construct encoding the engineered VP1/VP2 proteins ("AAV9 Transplant" or "AAV6/9 VP1/VP2"), we found that the proteolytic cleavage was abolished (FIG. 2A), the capsid protein ratio of VP1:VP2:VP3 was improved compared to the standard helper (FIG. 2B), and the potency of rAAV produced with the AAV9 Transplant helper increased nearly two-fold, compared to the Standard helper (FIG. 2C).

Figure 3A:
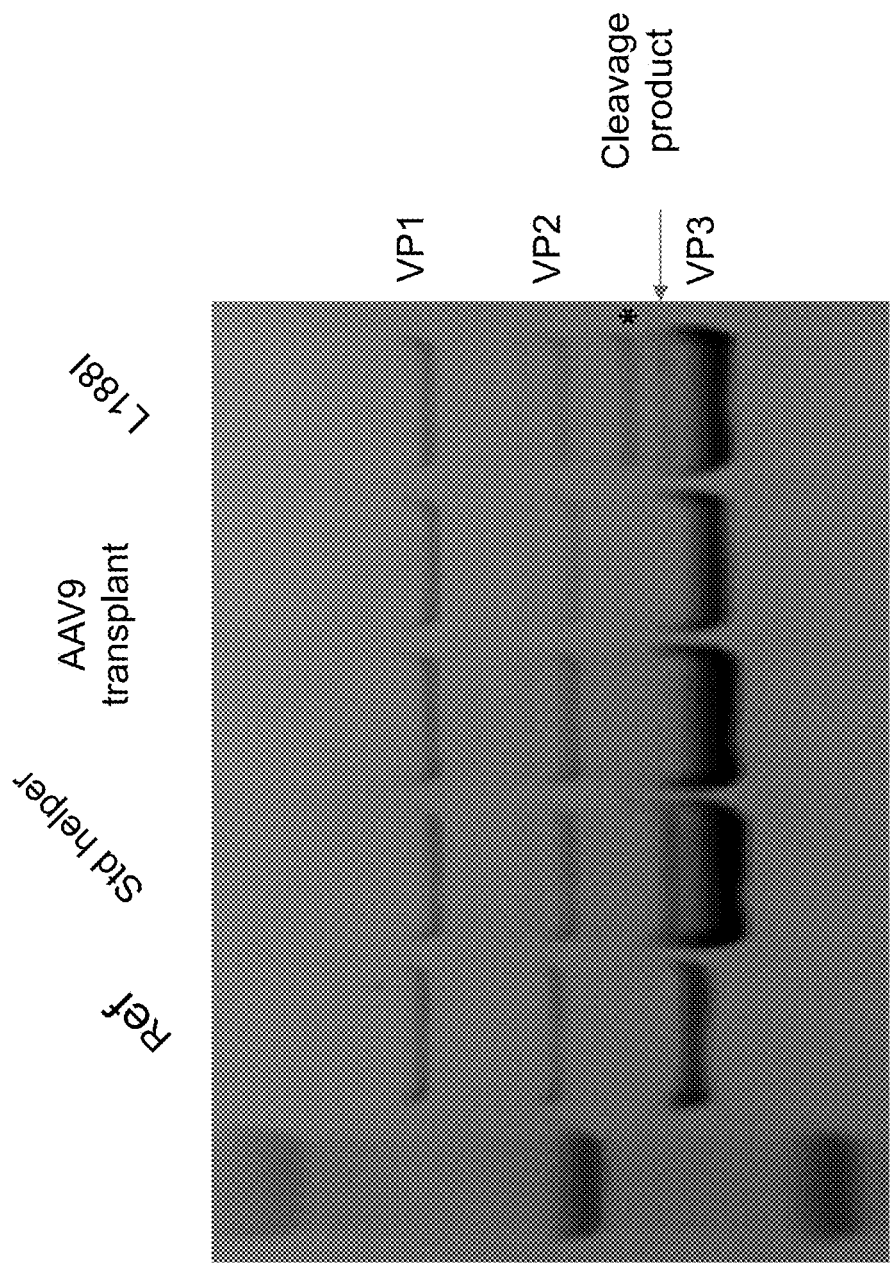
FIG. 3A is a photograph of a Coomassie-stained SDS-PAGE gel showing that the single point mutation L188I in AAV6 VP1/VP2 did not prevent proteolytic cleavage, as indicated by the protein species pointed to by the arrow. The asterisk denotes an additional cleavage product. Ref: rAAV6 produced in HEK293 cells. L188I: baculoviral AAV6 helper construct encoding AAV6 VP1/VP2 proteins with an L188I mutation (numbering in SEQ ID NO:1).

To dissect the elements in the transferred AAV9 sequence responsible for the improvement, we made a single L188I mutation in the AAV6 VP1/VP2 proteins. While the proteolytic cleavage between residues G189 and E190 appeared to decrease (FIG. 3A, arrow), a new band above it (FIG. 3A, *) appeared. Thus, the single L188I mutation did not solve the proteolytic problem.

Figure 3B:
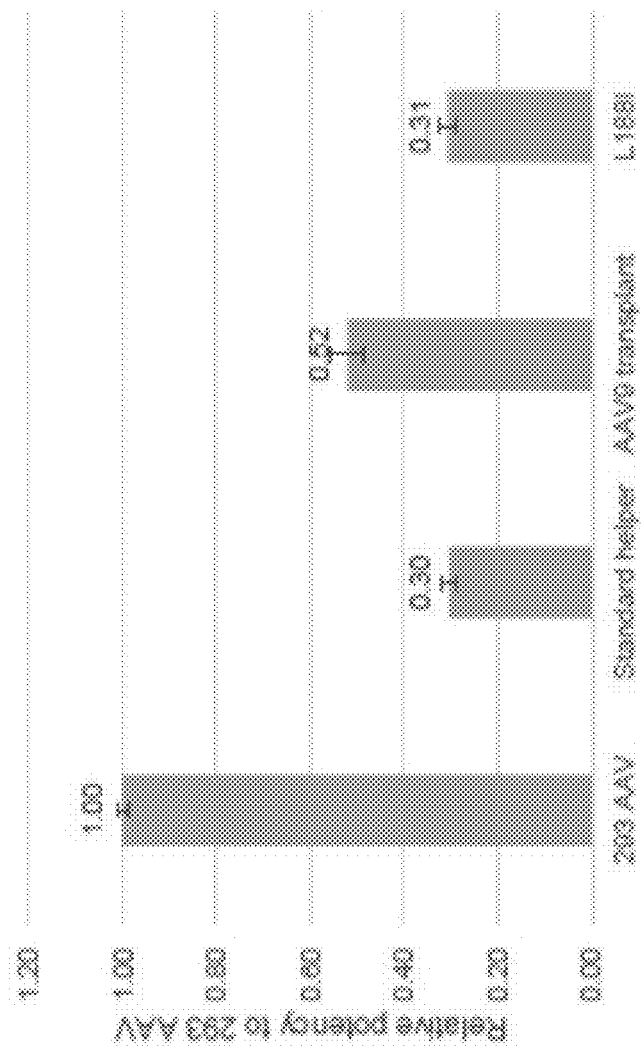
FIG. 3B is a bar graph showing the relative potency of rAAV6 produced with baculoviral helper having various AAV *cap* genes. Potency was calculated relative to 293 AAV.

To determine whether the L188I mutation impacted the potency of the rAAV6 produced from the helper, we produced rAAV containing the FIX cDNA and compared FIX expression levels from cells transduced with rAAV produced in 293 cells (293 AAV) or in 519 cells using the standard helper, AAV9 Transplant helper (expressing VP1/VP2 containing the 10 amino acid changes relative to the standard helper), or the L188I mutant helper. Relative potency was calculated with respect to 293 AAV. As shown in FIG. 3B, AAV produced with the AAV9 Transplant helper was significantly more potent than AAV produced with the L188I mutant helper (0.52 vs. 0.31).

Previous studies suggested that increasing the VP1 content of AAV capsids would lead to increased AAV potency, but most studies attempted to accomplish this by manipulating the start codon or the Kozak sequence near the start codon (Kohlbrenner et al., supra); Urabe et al., 2006, supra; and Kondratov et al., supra). Our work suggests that preventing proteolytic cleavage of VP1 is another viable approach to improving rAAV potency.

Figure 4A:
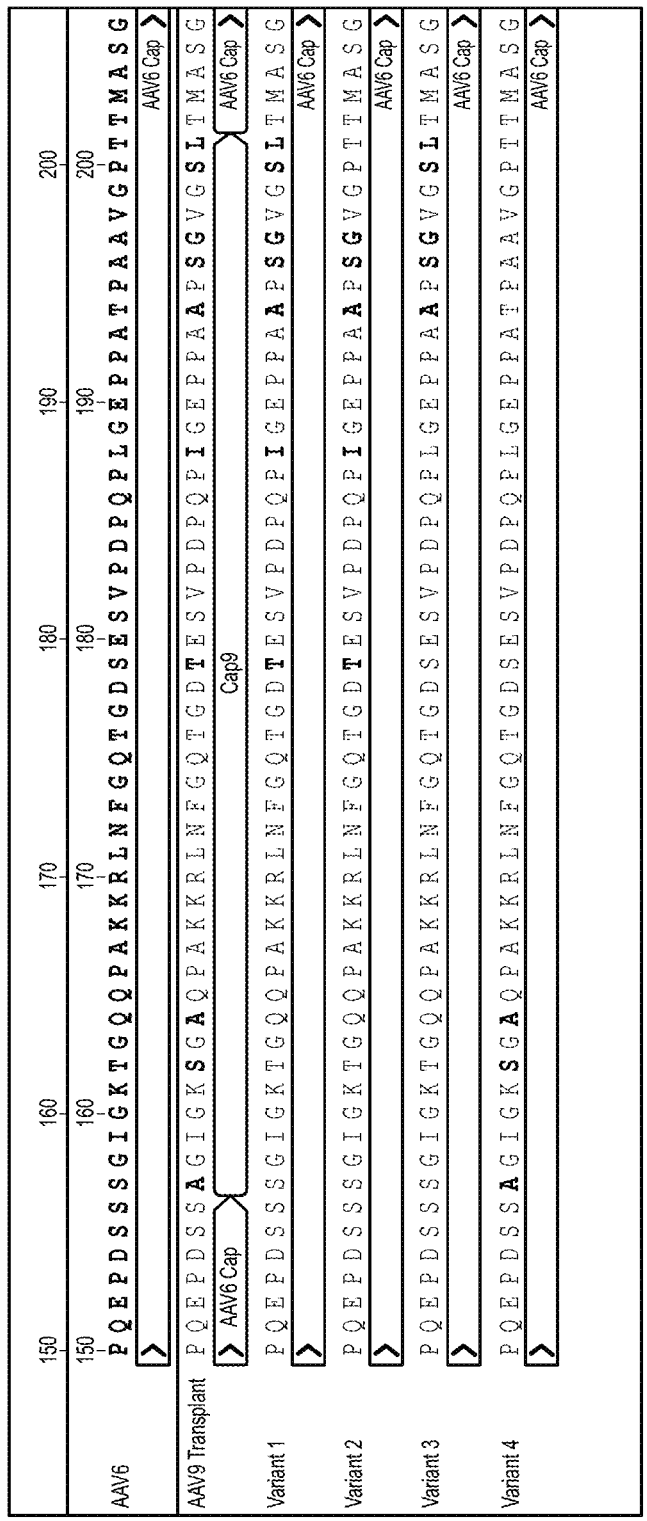
Figure 4B:
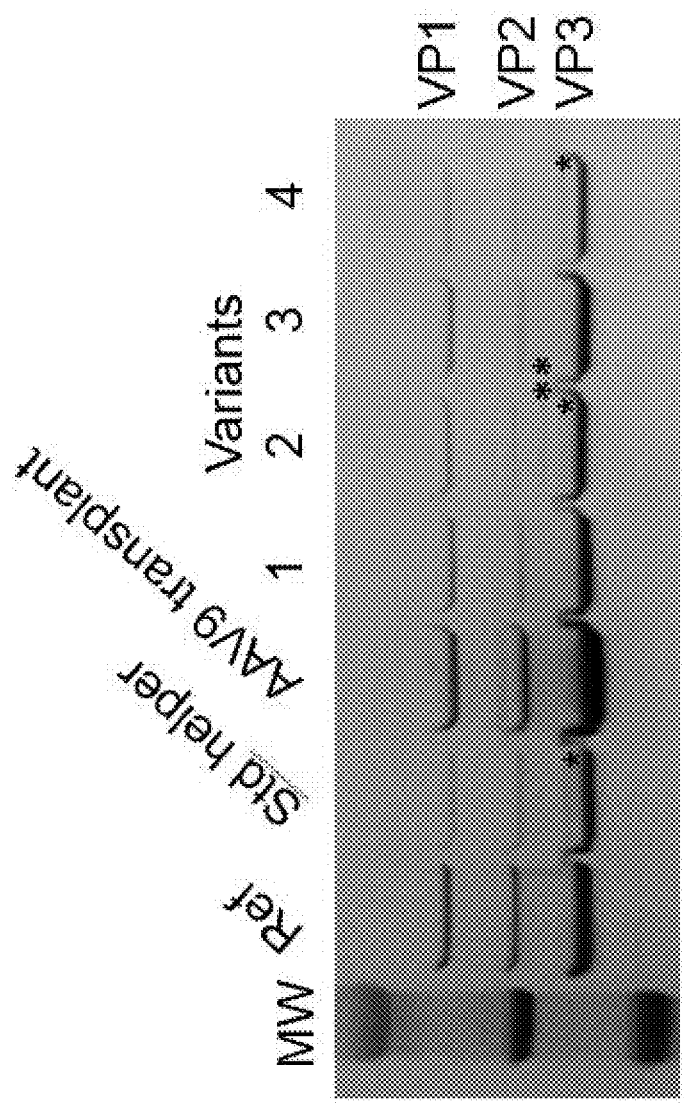
Figure 4C:
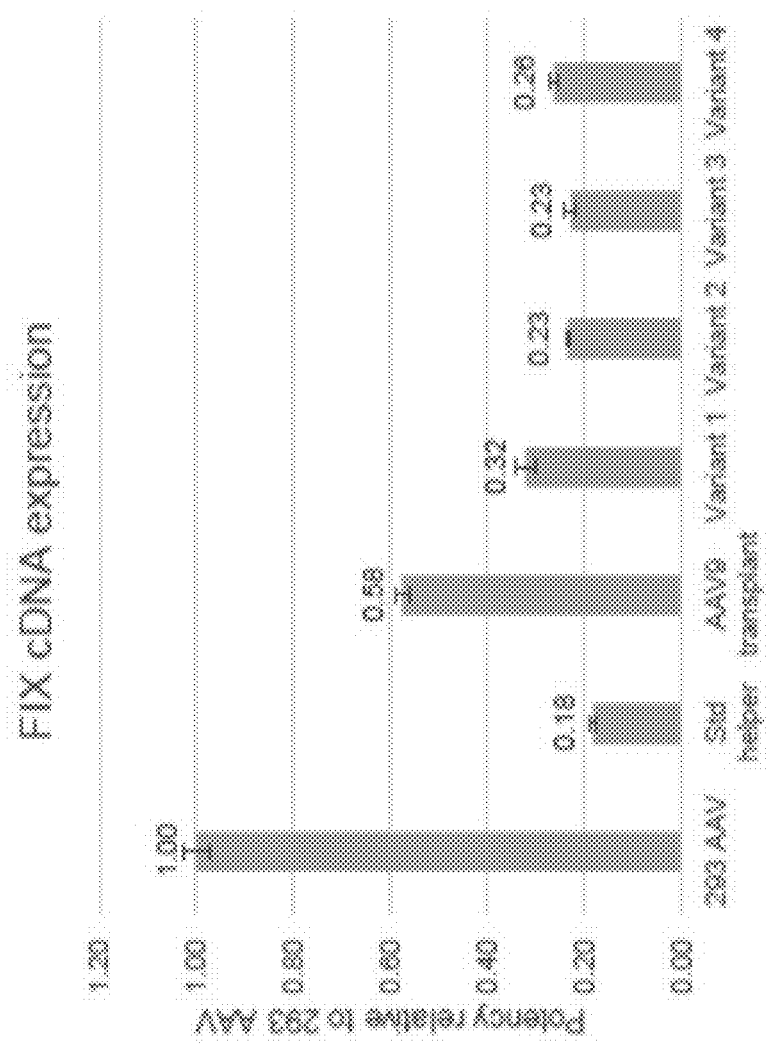
Figure 4D:
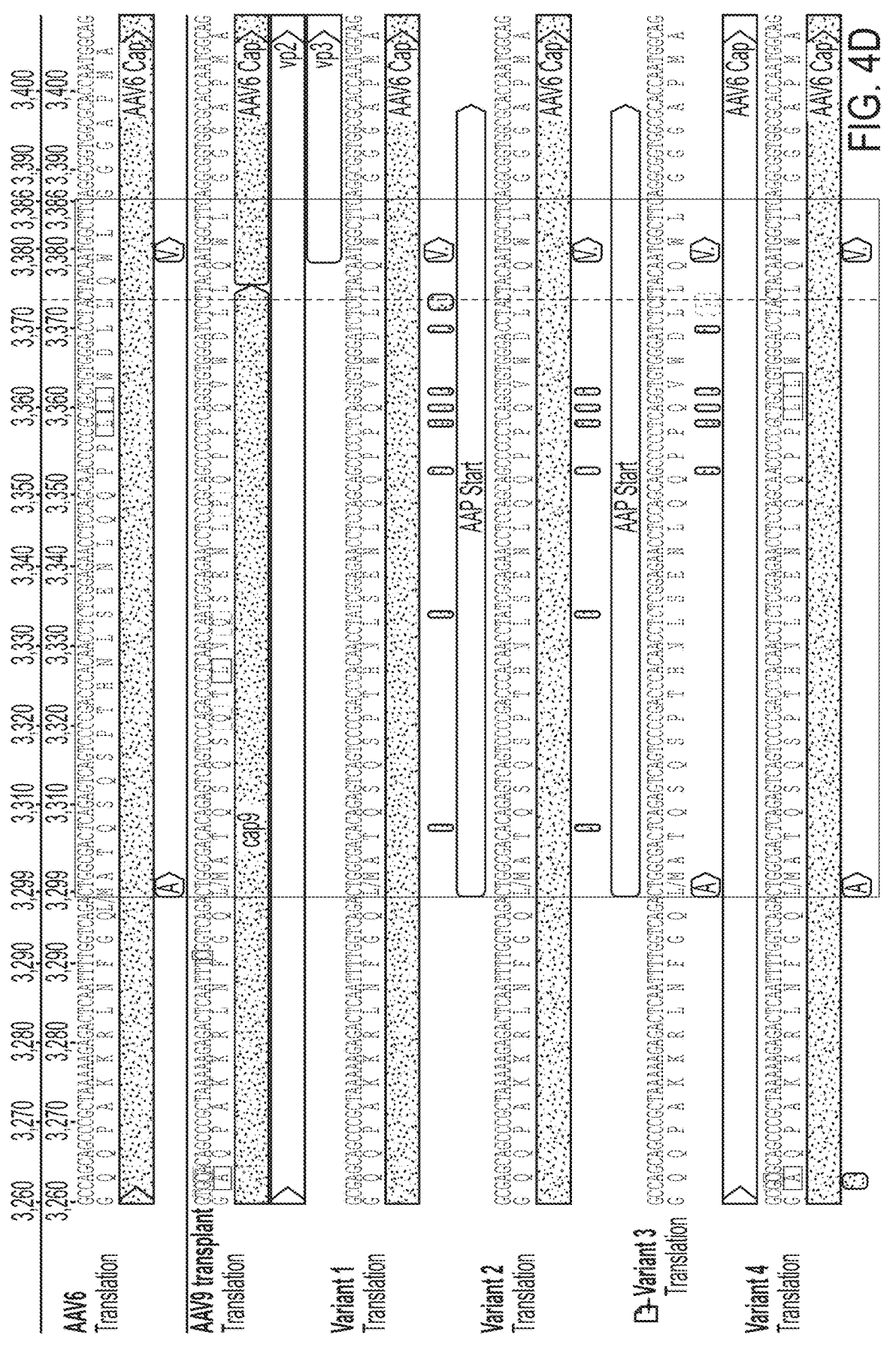
Figures 5A, 5B:
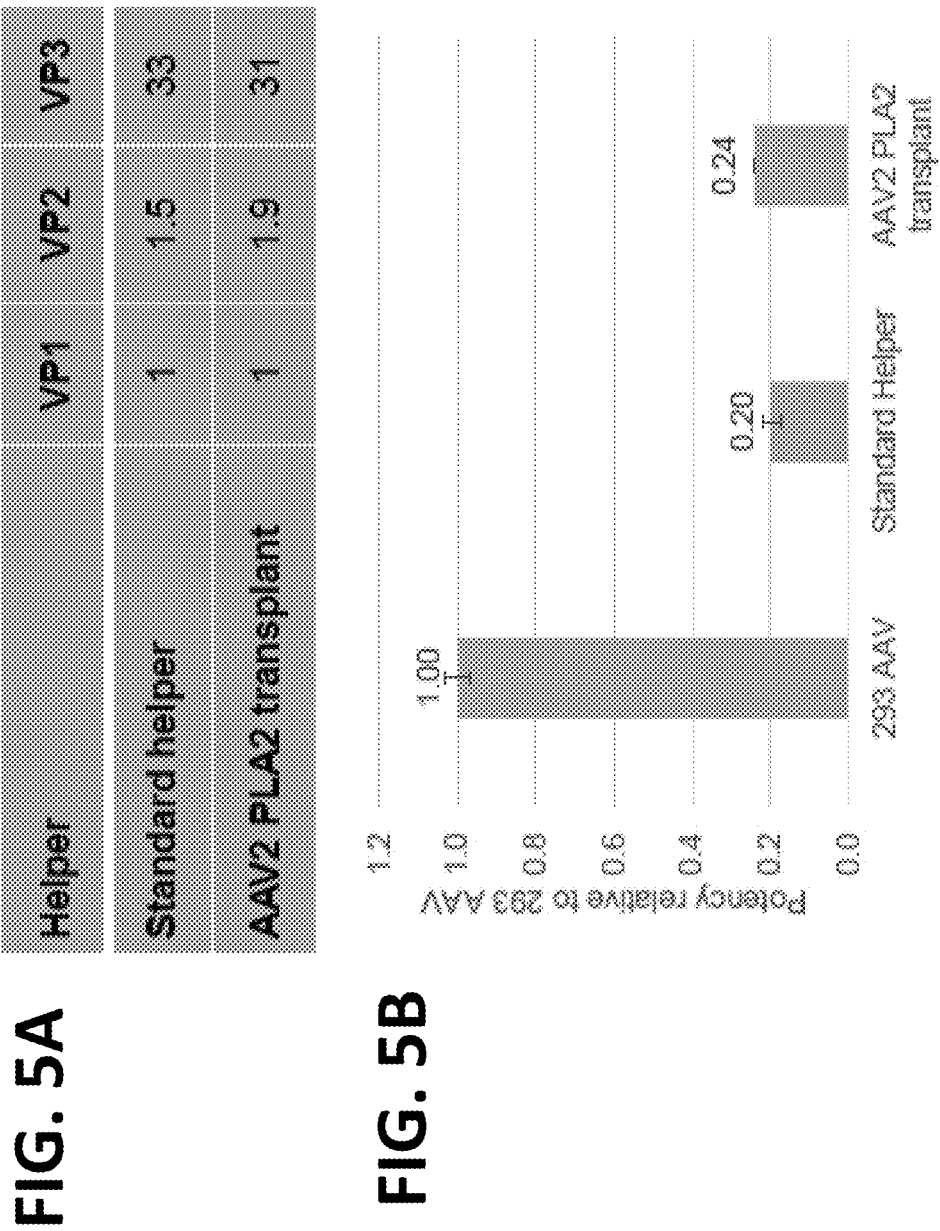
FIGS. 5A and 5B compare the capsid protein ratio and potency of rAAV6 produced with the Standard helper and rAAV6 produced with a baculoviral AAV6 helper construct containing an AAV2 PLA2 (phospholipase A2 domain) transplant ("AAV2 PLA2 transplant" or "AAV6/2 VP1"). The rAAV6 contained a FIX transgene.

We generated variants (Variants 1-4) of the AAV9 Transplant that contained subsets of the 10 amino acid changes in the AAV9 Transplant (FIG. 4A). As shown in FIG. 4B, while some mutations abolished the proteolytic cleavage (Variant 1 and 3), other mutations either did not abolish proteolytic cleavage (Variant 4) or resulted in an additional proteolytic cleavage (Variant 2). Furthermore, when the potency of these variants was compared to 293 AAV, the standard helper or AAV9 Transplant, no variant achieved equivalent potency to the AAV9 Transplant (FIG. 4C). Thus, although Variants 1 and 3 were not detectably cleaved in insect cells, these two variants did not have improved potency compared to rAAV made with the native AAV6 helper construct.

We noted that the AAV9 Transplant not only had mutated residues in VP1/VP2 relative to native AAV6 VP1/VP2, the engineered construct also had an altered open reading frame for AAP, resulting in the following point mutations relative to native AAP6: P8Q, H10L, L12Q, Q17P, L21Q and L22V (FIG. 4D). Variants 1-3 have only two mutations, L21Q and L22V. It appears that one or more of these mutations, e.g., one or more of P8Q, H10L, L12Q, and Q17P, contributed to the observed increase in potency of the rAAV made with the AAV9 Transplant helper construct.

Example 2: Improvement of Recombinant AAV Yield

Groups working with AAV5 and AAV8 production in the baculovirus-insect cell system reported that rAAV produced in insect cells transduced cells poorly compared to rAAV produced in 293 cells (Kohlbrenner et al., supra; and Urabe et al., supra). These groups transplanted the 134 or 142 amino acid N-terminal portion of the VP1 sequence from AAV2 into the AAV5 or AAV8 VP1 leader sequence and demonstrated that rAAV produced from these chimeric helpers had improved capsid protein ratios and potency with respect to rAAV produced in 293 cells. Id. Unfortunately, these studies did not identify the elements in the transplanted sequence that were responsible for the improvement.

The AAV VP1 leader sequence contains a phospholipase A2-like (PLA2) enzymatic domain, which is required for infection (see, e.g., Zadori et al., *Developmental Cell,* 1:291-302 (2001); and Girod et al., *J of General Virology,* 83:973-8 (2002)). To investigate the role of the PLA2 domain in rAAV's capsid protein ratio, potency, and yield, we transferred an amino acid sequence from AAV2 VP1's PLA2 domain (SEQ ID NO:6) to the baculoviral AAV6 helper, replacing the native AAV6 sequence (SEQ ID NO:5). The wildtype AAV6 and AAV2 sequences in this region (residues 52-97 of SEQ ID NO:1) are shown below, where the five amino acid changes relative to wildtype AAV6 after the AAV2 sequence transplant are boldfaced and boxed:

(SEQ ID NO: 5)

AAV6: YLGPFNGLDK GEPVNAADAA ALEHDKAYDQ QLKAGDNPYL RYNHAD (SEQ ID NO: 6)

AAV2: YLGPFNGLDK GEPVNEADAA ALEHDKAYDR QLDSGNPYL KYNHAD

We observed that there was no significant change in the capsid protein ratios between the Standard helper, which contained the cap gene sequence derived entirely from AAV6, and the chimeric baculovirus helper that contained the AAV2 PLA2 transplant ("AAV6/2 VP1") (FIG. 5A). There also was no significant difference in potency between rAAV6 produced with the Standard helper and with the chimeric AAV6/2 helper (FIG. 5B).

We did, however, observe a significant and reproducible four-fold increase in the yield of rAAV6 produced with the chimeric AAV6/2 helper, as compared to the Standard helper, as shown in Table 1 below, where average yield was calculated based on the yield derived the Standard helper, and N indicates the number of independent production samples. We have found that this result was independent of the sequence being packaged into the rAAV.

TABLE 1

| Helper Construct | Average Yield | N |
|---|---|---|
| Standard helper | 1.0 | 7 |
| Chimeric AAV6/2 helper | 3.9 | 7 |

Unexpectedly, rAAV6 production using the chimeric AAV6/2 helper resulted in a significant increase in yield compared to the Standard helper.

We applied the same strategy to a baculovirus AAV9 helper for producing rAAV9 capsid. We replaced the AAV9 VP1 PLA2 domain with that from AAV2 VP1 to generate AAV9/2 VP1. The wildtype AAV9 VP1 sequence (UniProtKB-Q6JC40 (Q6JC40_9VIRU)) is shown below, where the five amino acid residues differing from the corresponding ones in the AAV9/2 VP1 in the PLA2 domain are indicated with boldface and boxes:

(SEQ ID NO: 11)

1 MAADGYLPDW LEDNLSEGIR EWWALKPGAP QPKANQQHQD NARGLVLPGY KYLGPGNGLD

61 KGEPVNAADA AALEHDKAYD QQLKAGDNPY LKYNHADAEF QERLKEDTSF GGNLGRAVFQ

121 AKKRLLTPLG LVEEAAKTAP GKKRPVEQSP QEPDSSAGIG KSGAQPAKKR LNFGQTGDTE

181 SVPDPQPIGE PPAAPSGVGS LTMASGGGAP VADNNEGADG VGSSSGNWHC DSQWLGDRVI

241 TTSTRTWALP TYNNHLYKQI SNSTSGGSSN DNAYFGYSTP WGYFDFNRFH CHFSPRDWQR

301 LINNNWGFRP KRLNFKLFNI QVKEVTDNNG VKTIANNLTS TVQVFTDSDY QLPYVLGSAH

361 EGCLPPFPAD VFMIPQYGYL TLNDGSQAVG RSSFYCLEYF PSQMLRTGNN FQFSYEFENV

421 PFHSSYAHSQ SLDRLMNPLI DQYLYYLSKT INGSGQNQQT LKFSVAGPSN MAVQGRNYIP

```
481 GPSYRQQRVS TTVTQNNNSE FAWPGASSWA LNGRNSLMNP GPAMASHKEG EDRFFPLSGS

541 LIFGKQGTGR DNVDADKVMI TNEEEIKTTN PVATESYGQV ATNHQSAQAQ AQTGWVQNQG

601 ILPGMVWQDR DVYLQGPIWA KIPHTDGNFH PSPLMGGFGM KHPPPQILIK NTPVPADPPT

661 AFNKDKLNSF ITQYSTGQVS VEIEWELQKE NSKRWNPEIQ YTSNYYKSNN VEFAVNTEGV

721 YSEPRPIGTR YLTRNL
```

The wildtype AAV9 and AAV2 sequences in this region (residues 52-97 of SEQ ID NO:11) are shown below, where the five amino acid changes relative to wildtype AAV9 after the AAV2 sequence transplant are boldfaced and boxed:

```
                                            (SEQ ID NO: 12)
AAV9:    YLGPGNGLDK GEPVNAADAA ALEHDKAYDQ QLKAGDNPYL
         KYNHAD (SEQ ID NO: 6)
AAV2:    YLGP[F]NGLDK GEPVN[G]ADAA ALEHDKAYD[R] QL[DS]GDNPYL
         KYNHAD
```

We found that a chimeric helper construct expressing the AAV9/2 VP1 led to a three-fold increase in rAAV9 yield, as compared to the original AAV9 helper containing the native PLA2 domain (Table 2).

TABLE 2

| Helper Construct | Average Yield | N |
|---|---|---|
| Standard helper | 1.0 | 3 |
| Chimeric AAV9/2 helper | 2.9 | 3 |

Figure 6:
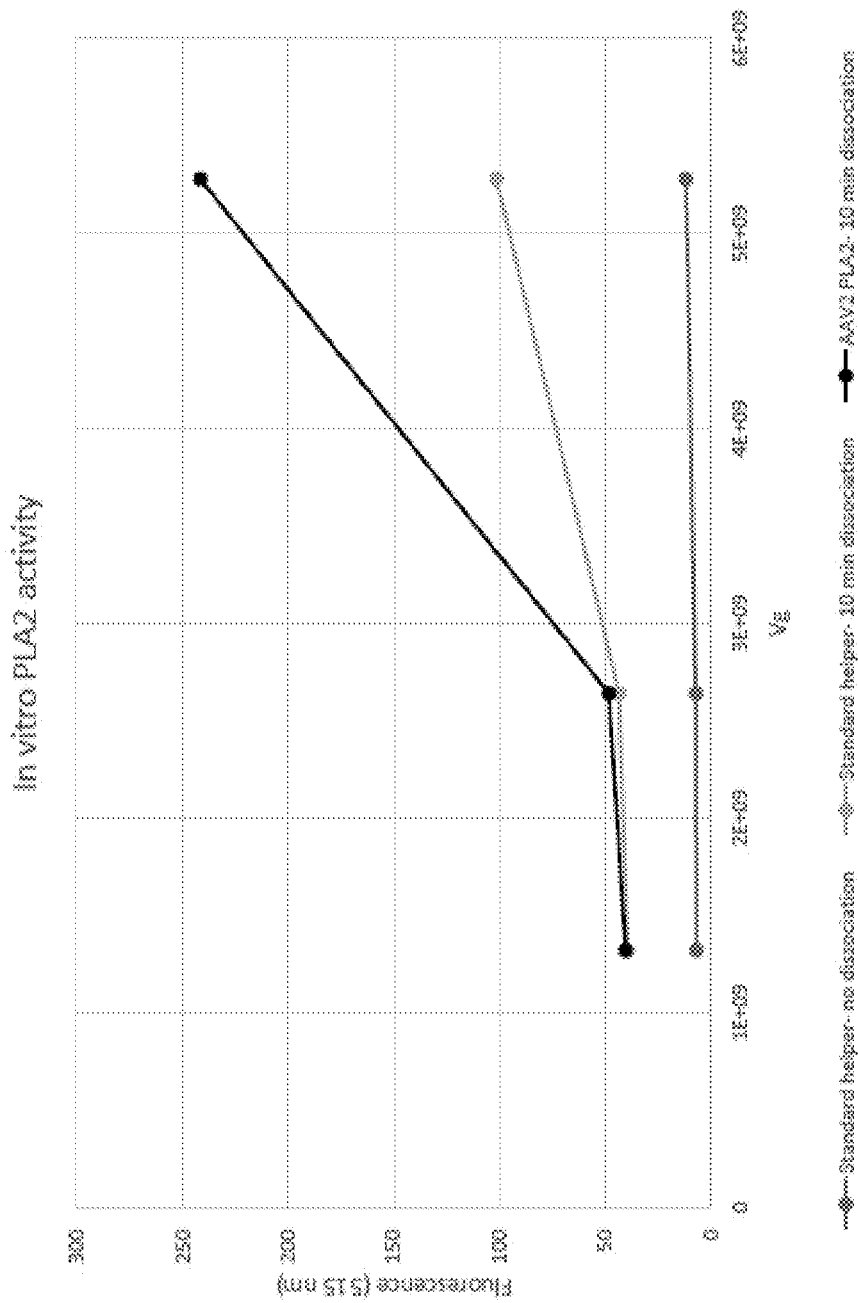
FIG. 6 is a graph comparing PLA2 activity in vitro. Vg: viral particles.

We also evaluated the PLA2 enzymatic activity of the AAV6/2 VP1. To do so, we used the ThermoFisher ENZCHEK® Phospholipase A2 Assay Kit (E10217). We dissociated the AAV capsids by incubating the viral preparation for 10 min at room temperature in 50 mM NaOH, neutralizing the sample with 100 mM HCl, and then assaying the sample for PLA2 activity according to manufacturer's instructions. Fluorescence emission of the enzyme substrate at 515 nm was recorded. The data show that compared to rAAV6 generated using the standard helper (with and without dissociation), rAAV6 generated with the AAV6/2 helper (helper containing the AAV2 PLA2 domain) had significantly higher PLA2 activity (FIG. 6).

These results suggest that the PLA2 domain possesses additional and previously unknown functions in AAV production, and these functions directly impact the yield in rAAV manufacturing. A helper virus that provides a more enzymatically active PLA2 can help improve rAAV yield in insect cells.

TABLE 3

| SEQ ID NO | Description |
|---|---|
| 1 | AAV6 VP1 amino acid sequence |
| 2 | AAV6 proteolytic site |
| 3 | AAV6 VP1/VP2 fragment |
| 4 | AAV9 VP1/VP2 fragment |
| 5 | AAV6 VP1 fragment |
| 6 | AAV2 VP1 fragment |
| 7 | AAV6/2/9 VP1 amino acid sequence |
| 8 | AAP6 residues 1-30 |
| 9 | AAP9 residues 1-30 |
| 10 | AAP6 amino acid sequence |
| 11 | AAV9 VP1 amino acid sequence |
| 12 | AAV9 VP1 fragment |
| 13 | Partial AAV6 cap nucleotide sequence |
| 14 | Partial AAV9 cap nucleotide sequence |
| 15 | AAV6 capsid protein fragment |
| 16 | AAV VP1/VP2 partial consensus sequence |
| 17 | AAV3B VP1/VP2 fragment |
| 18 | AAV5 VP1/VP2 fragment |
| 19 | AAV6 VP1/VP2 fragment |
| 20 | AAV8 VP1/VP2 fragment |
| 21 | AAV9 VP1/VP2 fragment |
| 22 | AAV VP1/VP2 partial consensus sequence |
| 23 | AAV1 and AAV6 VP1/VP2 fragment |
| 24 | AAV2 VP1/VP2 fragment |
| 25 | AAV3B VP1/VP2 fragment |
| 26 | AAV4 VP1/VP2 fragment |
| 27 | AAV7 VP1/VP2 fragment |
| 28 | AAV8 VP1/VP2 fragment |
| 29 | AAV9 VP1/VP2 fragment |
| 30 | AAV10 VP1/VP2 fragment |
| 31 | AAV11 VP1/VP2 fragment |
| 32 | AAV6 VP1/VP2 fragment |
| 33 | AAV6/9 VP1/VP2 fragment (AAV9 transplant) |
| 34 | AAV9 transplant variant 1 |
| 35 | AAV9 transplant variant 2 |
| 36 | AAV9 transplant variant 3 |
| 37 | AAV9 transplant variant 4 |
| 38 | Partial AAV6 cap nucleotide sequence |
| 39 | AAV6 AAP fragment |
| 40 | Partial AAV9 transplant cap nucleotide sequence |
| 41 | AAV9 transplant AAP fragment |
| 42 | Partial AAV9 transplant variant 1 cap nucleotide sequence |
| 43 | AAV9 transplant variant 1, 2, and 3 AAP fragment |
| 44 | Partial AAV9 transplant variant 2 cap nucleotide sequence |
| 45 | Partial AAV9 transplant variant 3 cap nucleotide sequence |
| 46 | Partial AAV9 transplant variant 4 cap nucleotide sequence |
| 47 | AAV9 transplant variant 4 AAP fragment |
| 48 | AAV AAP partial consensus sequence |
| 49 | AAV1 AAP fragment |
| 50 | AAV2 AAP fragment |
| 51 | AAV3B AAP fragment |
| 52 | AAV4 AAP fragment |
| 53 | AAV7 AAP fragment |
| 54 | AAV8 AAP fragment |
| 55 | AAV10 AAP fragment |
| 56 | AAV11 AAP fragment |

What is claimed is:

1. A nucleic acid construct comprising a nucleotide sequence encoding adeno-associated virus (AAV) VP1, VP2, and VP3 proteins, wherein the VP1 protein and the VP2 protein comprise two or more mutations selected from a first group consisting of S157A, T162S, Q164A, S179T, L188I, T194A, A196S, A197G, P200S, and T201L, (numbering according to SEQ ID NO:1) relative to wildtype VP1 and VP2 proteins.

2. The nucleic acid construct of claim 1, wherein the VP1 protein and the VP2 protein comprise all of the mutations in said first group.

3. The nucleic acid construct of claim 1, wherein the VP1 protein further comprises one or more mutations at residues 67, 81, 84, 85, and 92 relative to wildtype VP1 protein (numbering according to SEQ ID NO:1).

4. The nucleic acid construct of claim 3, wherein the VP1 protein comprises one or more mutations selected from the second group consisting of A67E, Q81R, K84D, A85S, and R92K.

5. The nucleic acid construct of claim 4, wherein the VP1 protein comprises all of the mutations in said second group.

6. The nucleic acid construct of claim 1, wherein the VP1 protein and the VP2 protein are identical to the VP1 protein and the VP2 protein, respectively, of wildtype AAV6 but for the mutations.

7. The nucleic acid construct of claim 1, wherein the nucleotide sequence also comprises an open reading frame coding for assembly-activating protein (AAP), wherein the AAP comprises one or more mutations at residues 8, 10, 12, 17, 21, and 22 (numbering according to SEQ ID NO:10) relative to wildtype AAP protein.

8. The nucleic acid construct of claim 7, wherein the AAP comprises one or more AAP mutations selected from the third group consisting of P8Q, H10L, L12Q, Q17P, L21Q, and L22V.

9. The nucleic acid construct of claim 8, wherein the AAP is identical to wildtype AAP of AAV6 but for the AAP mutations.

10. The nucleic acid construct of claim 9, wherein the VP1 protein and the VP2 protein are derived from AAV6 and comprise mutations S157A, T162S, Q164A, S179T, L188I, T194A, A196S, A197G, P200S, and T201L relative to AAV6 VP1 and VP2 proteins.

11. The nucleic acid construct of claim 9, wherein the construct comprises a coding sequence for SEQ ID NO:7, with or without the first amino acid.

12. An insect cell comprising the nucleic acid construct of claim 1.

13. A recombinant AAV virion comprising (i) a genome having a transgene of interest flanked by a pair of AAV Inverted Terminal Repeats (ITR), and (ii) a capsid assembled from the VP1, or both VP1 and VP2 proteins, expressed from the nucleic acid construct of claim 1.

14. A recombinant AAV virion produced in the insect cell of claim 12.

15. A method of producing a recombinant AAV virion, comprising:
- providing the insect cell of claim 12, wherein the insect cell also expresses AAV Rep proteins and comprises the coding sequence for an AAV vector comprising a transgene of interest flanked by a pair of AAV Inverted Terminal Repeats (ITR),
- culturing the insect cell under conditions to allow expression of the VP1, VP2, VP3 proteins, replication of the AAV vector, and packaging of the AAV vector into a capsid assembled from the expressed VP1, VP2, and VP3 proteins, and
- recovering the packaged capsid.

16. A recombinant AAV virion produced by the method of claim 15.

* * * * *

SEQUENCE LISTING

<160> NUMBER OF SEQ ID NOS: 56

<210> SEQ ID NO 1
<211> LENGTH: 736
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met, Thr, Leu or Val

<400> SEQUENCE: 1

Xaa Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

```
Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 2
<211> LENGTH: 10
```

```
<212> TYPE: PRT
<213> ORGANISM: Adeno-associated virus

<400> SEQUENCE: 2

Pro Gln Pro Leu Gly Glu Pro Pro Ala Thr
1               5                   10

<210> SEQ ID NO 3
<211> LENGTH: 45
<212> TYPE: PRT
<213> ORGANISM: Adeno-associated virus

<400> SEQUENCE: 3

Ser Gly Ile Gly Lys Thr Gly Gln Gln Pro Ala Lys Lys Arg Leu Asn
1               5                   10                  15

Phe Gly Gln Thr Gly Asp Ser Glu Ser Val Pro Asp Pro Gln Pro Leu
            20                  25                  30

Gly Glu Pro Pro Ala Thr Pro Ala Ala Val Gly Pro Thr
        35                  40                  45

<210> SEQ ID NO 4
<211> LENGTH: 45
<212> TYPE: PRT
<213> ORGANISM: Adeno-associated virus

<400> SEQUENCE: 4

Ala Gly Ile Gly Lys Ser Gly Ala Gln Pro Ala Lys Lys Arg Leu Asn
1               5                   10                  15

Phe Gly Gln Thr Gly Asp Thr Glu Ser Val Pro Asp Pro Gln Pro Ile
            20                  25                  30

Gly Glu Pro Pro Ala Ala Pro Ser Gly Val Gly Ser Leu
        35                  40                  45

<210> SEQ ID NO 5
<211> LENGTH: 46
<212> TYPE: PRT
<213> ORGANISM: Adeno-associated virus

<400> SEQUENCE: 5

Tyr Leu Gly Pro Phe Asn Gly Leu Asp Lys Gly Glu Pro Val Asn Ala
1               5                   10                  15

Ala Asp Ala Ala Ala Leu Glu His Asp Lys Ala Tyr Asp Gln Gln Leu
            20                  25                  30

Lys Ala Gly Asp Asn Pro Tyr Leu Arg Tyr Asn His Ala Asp
        35                  40                  45

<210> SEQ ID NO 6
<211> LENGTH: 46
<212> TYPE: PRT
<213> ORGANISM: Adeno-associated virus

<400> SEQUENCE: 6

Tyr Leu Gly Pro Phe Asn Gly Leu Asp Lys Gly Glu Pro Val Asn Glu
1               5                   10                  15

Ala Asp Ala Ala Ala Leu Glu His Asp Lys Ala Tyr Asp Arg Gln Leu
            20                  25                  30

Asp Ser Gly Asp Asn Pro Tyr Leu Lys Tyr Asn His Ala Asp
        35                  40                  45

<210> SEQ ID NO 7
<211> LENGTH: 736
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp Arg
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 8
<211> LENGTH: 30
<212> TYPE: PRT
<213> ORGANISM: Adeno-associated virus

<400> SEQUENCE: 8

Met Ala Thr Gln Ser Gln Ser Pro Thr His Asn Leu Ser Glu Asn Leu
1               5                   10                  15

Gln Gln Pro Pro Leu Leu Trp Asp Leu Leu Gln Trp Leu Gln

<210> SEQ ID NO 9
<211> LENGTH: 30
<212> TYPE: PRT
<213> ORGANISM: Adeno-associated virus

<400> SEQUENCE: 9

Met Ala Thr Gln Ser Gln Ser Gln Thr Leu Asn Gln Ser Glu Asn Leu
1               5                   10                  15

Pro Gln Pro Pro Gln Val Trp Asp Leu Leu Gln Trp Leu Gln
            20                  25                  30

<210> SEQ ID NO 10
<211> LENGTH: 196
<212> TYPE: PRT
<213> ORGANISM: Adeno-associated virus

<400> SEQUENCE: 10

Met Ala Thr Gln Ser Gln Ser Pro Thr His Asn Leu Ser Glu Asn Leu
1               5                   10                  15

Gln Gln Pro Pro Leu Leu Trp Asp Leu Leu Gln Trp Leu Gln Ala Val
            20                  25                  30

Ala His Gln Trp Gln Thr Ile Thr Lys Ala Pro Thr Glu Trp Val Met
        35                  40                  45

Pro Gln Glu Ile Gly Ile Ala Ile Pro His Gly Trp Ala Thr Glu Ser
    50                  55                  60

Ser Pro Pro Ala Pro Glu His Gly Pro Cys Pro Pro Ile Thr Thr Thr
65                  70                  75                  80

Ser Thr Ser Lys Ser Pro Val Leu Gln Arg Gly Pro Ala Thr Thr
                85                  90                  95

Thr Thr Ser Ala Thr Ala Pro Pro Gly Gly Ile Leu Ile Ser Thr Asp
            100                 105                 110

Ser Thr Ala Ile Ser His His Val Thr Gly Ser Asp Ser Ser Thr Thr
        115                 120                 125

Ile Gly Asp Ser Gly Pro Arg Asp Ser Thr Ser Ser Ser Ser Thr Ser
130                 135                 140

Lys Ser Arg Arg Ser Arg Arg Met Met Ala Ser Arg Pro Ser Leu Ile
145                 150                 155                 160

Thr Leu Pro Ala Arg Phe Lys Ser Ser Arg Thr Arg Ser Thr Ser Cys
                165                 170                 175

Arg Thr Ser Ser Ala Leu Arg Thr Arg Ala Ala Ser Leu Arg Ser Arg
            180                 185                 190

Arg Thr Cys Ser
        195

<210> SEQ ID NO 11
<211> LENGTH: 736
<212> TYPE: PRT
<213> ORGANISM: Adeno-associated virus

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

```
Gly Tyr Lys Tyr Leu Gly Pro Gly Asn Gly Leu Asp Lys Gly Glu Pro
    50                  55                  60
Val Asn Ala Ala Asp Ala Ala Leu Glu His Asp Lys Ala Tyr Asp
 65              70                  75                  80
Gln Gln Leu Lys Ala Gly Asp Asn Pro Tyr Leu Lys Tyr Asn His Ala
             85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
```

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
        500                 505                 510

Gly Arg Asn Ser Leu Met Asn Pro Gly Pro Ala Met Ala Ser His Lys
    515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 12
<211> LENGTH: 46
<212> TYPE: PRT
<213> ORGANISM: Adeno-associated virus

<400> SEQUENCE: 12

Tyr Leu Gly Pro Gly Asn Gly Leu Asp Lys Gly Glu Pro Val Asn Ala
1               5                   10                  15

Ala Asp Ala Ala Ala Leu Glu His Asp Lys Ala Tyr Asp Gln Gln Leu
            20                  25                  30

Lys Ala Gly Asp Asn Pro Tyr Leu Lys Tyr Asn His Ala Asp
        35                  40                  45

<210> SEQ ID NO 13
<211> LENGTH: 183
<212> TYPE: DNA
<213> ORGANISM: Adeno-associated virus

<400> SEQUENCE: 13
aagagccaga ctcctcctcg ggcattggca agacaggcca gcagcccgct aaaaagagac     60
tcaattttgg tcagactggc gactcagagt cagtccccga cccacaacct ctcggagaac    120

-continued

```
ctccagcaac cccgctgct gtgggaccta ctacaatggc ttcaggcggt ggcgcaccaa    180
tgg                                                                 183
```

<210> SEQ ID NO 14
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
aagagccaga ctcctccgcg ggtattggca atcgggtgc acagcccgct aaaaagagac    60
tcaatttcgg tcagactggc gacacagagt cagtcccaga ccctcaacca atcggagaac   120
ctcccgcagc cccctcaggt gtgggatctc ttacaatggc ttcaggcggt ggcgcaccaa   180
tgg                                                                 183
```

<210> SEQ ID NO 15
<211> LENGTH: 5
<212> TYPE: PRT
<213> ORGANISM: Adeno-associated virus

<400> SEQUENCE: 15

```
Glu Pro Pro Ala Thr
1               5
```

<210> SEQ ID NO 16
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Arg or Lys
<220> FEATURE:
<221> NAME/KEY: MOD_RES
<222> LOCATION: (44)..(44)
<223> OTHER INFORMATION: Ser, Ala or Gly
<220> FEATURE:
<221> NAME/KEY: MOD_RES
<222> LOCATION: (47)..(47)
<223> OTHER INFORMATION: Ser, Ala or Pro

<400> SEQUENCE: 16

```
Asp Ser Ser Ser Gly Ile Gly Lys Ser Gly Gln Gln Pro Ala Xaa Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Ala Pro Ser Xaa Val Gly Xaa Asn
        35                  40                  45

Thr Met Ala Ser
    50
```

<210> SEQ ID NO 17
<211> LENGTH: 52
<212> TYPE: PRT
<213> ORGANISM: Adeno-associated virus

<400> SEQUENCE: 17

```
Asp Ser Ser Ser Gly Val Gly Lys Ser Gly Lys Gln Pro Ala Arg Lys
```

```
                1               5                  10                  15
Arg Leu Asn Phe Gly Gln Thr Gly Asp Ser Glu Ser Val Pro Asp Pro
                20                  25                  30

Gln Pro Leu Gly Glu Pro Pro Ala Ala Pro Thr Ser Leu Gly Ser Asn
        35                  40                  45

Thr Met Ala Ser
        50

<210> SEQ ID NO 18
<211> LENGTH: 44
<212> TYPE: PRT
<213> ORGANISM: Adeno-associated virus

<400> SEQUENCE: 18

Lys Lys Ala Arg Thr Glu Glu Asp Ser Lys Pro Ser Thr Ser Ser Asp
1               5                   10                  15

Ala Glu Ala Gly Pro Ser Gly Ser Gln Gln Leu Gln Ile Pro Ala Gln
                20                  25                  30

Pro Ala Ser Ser Leu Gly Ala Asp Thr Met Ser Ala
        35                  40

<210> SEQ ID NO 19
<211> LENGTH: 52
<212> TYPE: PRT
<213> ORGANISM: Adeno-associated virus

<400> SEQUENCE: 19

Asp Ser Ser Ser Gly Ile Gly Lys Thr Gly Gln Gln Pro Ala Lys Lys
1               5                   10                  15

Arg Leu Asn Phe Gly Gln Thr Gly Asp Ser Glu Ser Val Pro Asp Pro
                20                  25                  30

Gln Pro Leu Gly Glu Pro Pro Ala Thr Pro Ala Ala Val Gly Pro Thr
        35                  40                  45

Thr Met Ala Ser
        50

<210> SEQ ID NO 20
<211> LENGTH: 52
<212> TYPE: PRT
<213> ORGANISM: Adeno-associated virus

<400> SEQUENCE: 20

Asp Ser Ser Thr Gly Ile Gly Lys Lys Gly Gln Gln Pro Ala Arg Lys
1               5                   10                  15

Arg Leu Asn Phe Gly Gln Thr Gly Asp Ser Glu Ser Val Pro Asp Pro
                20                  25                  30

Gln Pro Leu Gly Glu Pro Pro Ala Ala Pro Ser Gly Val Gly Pro Asn
        35                  40                  45

Thr Met Ala Ala
        50

<210> SEQ ID NO 21
<211> LENGTH: 52
<212> TYPE: PRT
<213> ORGANISM: Adeno-associated virus

<400> SEQUENCE: 21

Asp Ser Ser Ala Gly Ile Gly Lys Ser Gly Ala Gln Pro Ala Lys Lys
1               5                   10                  15
```

Arg Leu Asn Phe Gly Gln Thr Gly Asp Thr Glu Ser Val Pro Asp Pro
            20                  25                  30

Gln Pro Ile Gly Glu Pro Pro Ala Ala Pro Ser Gly Val Gly Ser Leu
        35                  40                  45

Thr Met Ala Ser
    50

<210> SEQ ID NO 22
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys or Arg

<400> SEQUENCE: 22

Asp Ser Ser Gly Ile Gly Lys Lys Gly Gln Gln Pro Ala Xaa Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Ala Pro Ser Gly Val Gly Ser Asn
        35                  40                  45

Thr Met Ala
    50

<210> SEQ ID NO 23
<211> LENGTH: 51
<212> TYPE: PRT
<213> ORGANISM: Adeno-associated virus

<400> SEQUENCE: 23

Asp Ser Ser Gly Ile Gly Lys Thr Gly Gln Gln Pro Ala Lys Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Thr Pro Ala Ala Val Gly Pro Thr
        35                  40                  45

Thr Met Ala
    50

<210> SEQ ID NO 24
<211> LENGTH: 51
<212> TYPE: PRT
<213> ORGANISM: Adeno-associated virus

<400> SEQUENCE: 24

Asp Ser Ser Gly Thr Gly Lys Ala Gly Gln Gln Pro Ala Arg Lys
1               5                   10                  15

Arg Leu Asn Phe Gly Gln Thr Gly Asp Ala Asp Ser Val Pro Asp Pro
            20                  25                  30

Gln Pro Leu Gly Gln Pro Pro Ala Ala Pro Ser Gly Leu Gly Thr Asn
        35                  40                  45

Thr Met Ala
    50

<210> SEQ ID NO 25
<211> LENGTH: 51

```
<212> TYPE: PRT
<213> ORGANISM: Adeno-associated virus

<400> SEQUENCE: 25

Asp Ser Ser Gly Val Gly Lys Ser Gly Lys Gln Pro Ala Arg Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Ala Pro Thr Ser Leu Gly Ser Asn
        35                  40                  45

Thr Met Ala
    50

<210> SEQ ID NO 26
<211> LENGTH: 46
<212> TYPE: PRT
<213> ORGANISM: Adeno-associated virus

<400> SEQUENCE: 26

Asp Ser Thr Gly Ile Gly Lys Lys Gly Lys Gln Pro Ala Lys Lys
1               5                   10                  15

Lys Leu Val Phe Glu Asp Glu Thr Gly Ala Gly Asp Gly Pro Pro Glu
            20                  25                  30

Gly Ser Thr Ser Gly Ala Met Ser Asp Asp Ser Glu Met Arg
        35                  40                  45

<210> SEQ ID NO 27
<211> LENGTH: 51
<212> TYPE: PRT
<213> ORGANISM: Adeno-associated virus

<400> SEQUENCE: 27

Asp Ser Ser Thr Gly Ile Gly Lys Lys Gly Gln Gln Pro Ala Arg Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Ala Pro Ser Ser Val Gly Ser Gly
        35                  40                  45

Thr Val Ala
    50

<210> SEQ ID NO 28
<211> LENGTH: 51
<212> TYPE: PRT
<213> ORGANISM: Adeno-associated virus

<400> SEQUENCE: 28

Asp Ser Thr Gly Ile Gly Lys Lys Gly Gln Gln Pro Ala Arg Lys
1               5                   10                  15

Arg Leu Asn Phe Gly Gln Thr Gly Asp Ser Glu Ser Val Pro Asp Pro
            20                  25                  30

Gln Pro Leu Gly Glu Pro Pro Ala Ala Pro Ser Gly Val Gly Pro Asn
        35                  40                  45

Thr Met Ala
    50

<210> SEQ ID NO 29
<211> LENGTH: 51
<212> TYPE: PRT
<213> ORGANISM: Adeno-associated virus
```

-continued

```
<400> SEQUENCE: 29

Asp Ser Ser Ala Gly Ile Gly Lys Ser Gly Ala Gln Pro Ala Lys Lys
1               5                   10                  15

Arg Leu Asn Phe Gly Gln Thr Gly Asp Thr Glu Ser Val Pro Asp Pro
            20                  25                  30

Gln Pro Ile Gly Glu Pro Pro Ala Ala Pro Ser Gly Val Gly Ser Leu
        35                  40                  45

Thr Met Ala
    50

<210> SEQ ID NO 30
<211> LENGTH: 51
<212> TYPE: PRT
<213> ORGANISM: Adeno-associated virus

<400> SEQUENCE: 30

Asp Ser Ser Thr Gly Ile Gly Lys Lys Gly Gln Gln Pro Ala Lys Lys
1               5                   10                  15

Arg Leu Asn Phe Gly Gln Thr Gly Glu Ser Glu Ser Val Pro Asp Pro
            20                  25                  30

Gln Pro Ile Gly Glu Pro Pro Ala Gly Pro Ser Gly Leu Gly Ser Gly
        35                  40                  45

Thr Met Ala
    50

<210> SEQ ID NO 31
<211> LENGTH: 46
<212> TYPE: PRT
<213> ORGANISM: Adeno-associated virus

<400> SEQUENCE: 31

Asp Ser Ser Ser Gly Ile Gly Lys Lys Gly Lys Gln Pro Ala Arg Lys
1               5                   10                  15

Arg Leu Asn Phe Glu Glu Asp Thr Gly Ala Gly Asp Gly Pro Pro Glu
            20                  25                  30

Gly Ser Asp Thr Ser Ala Met Ser Ser Asp Ile Glu Met Arg
        35                  40                  45

<210> SEQ ID NO 32
<211> LENGTH: 57
<212> TYPE: PRT
<213> ORGANISM: Adeno-associated virus

<400> SEQUENCE: 32

Pro Gln Glu Pro Asp Ser Ser Ser Gly Ile Gly Lys Thr Gly Gln Gln
1               5                   10                  15

Pro Ala Lys Lys Arg Leu Asn Phe Gly Gln Thr Gly Asp Ser Glu Ser
            20                  25                  30

Val Pro Asp Pro Gln Pro Leu Gly Glu Pro Pro Ala Thr Pro Ala Ala
        35                  40                  45

Val Gly Pro Thr Thr Met Ala Ser Gly
    50                  55

<210> SEQ ID NO 33
<211> LENGTH: 57
<212> TYPE: PRT
<213> ORGANISM: Artificial Sequence
<220> FEATURE:
<223> OTHER INFORMATION: Description of Artificial Sequence: Synthetic
```

-continued

```
      polypeptide

<400> SEQUENCE: 33

Pro Gln Glu Pro Asp Ser Ser Ala Gly Ile Gly Lys Ser Gly Ala Gln
1               5                   10                  15

Pro Ala Lys Lys Arg Leu Asn Phe Gly Gln Thr Gly Asp Thr Glu Ser
            20                  25                  30

Val Pro Asp Pro Gln Pro Ile Gly Glu Pro Pro Ala Ala Pro Ser Gly
        35                  40                  45

Val Gly Ser Leu Thr Met Ala Ser Gly
    50                  55

<210> SEQ ID NO 34
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Pro Gln Glu Pro Asp Ser Ser Ser Gly Ile Gly Lys Thr Gly Gln Gln
1               5                   10                  15

Pro Ala Lys Lys Arg Leu Asn Phe Gly Gln Thr Gly Asp Thr Glu Ser
            20                  25                  30

Val Pro Asp Pro Gln Pro Ile Gly Glu Pro Pro Ala Ala Pro Ser Gly
        35                  40                  45

Val Gly Ser Leu Thr Met Ala Ser Gly
    50                  55

<210> SEQ ID NO 35
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Pro Gln Glu Pro Asp Ser Ser Ser Gly Ile Gly Lys Thr Gly Gln Gln
1               5                   10                  15

Pro Ala Lys Lys Arg Leu Asn Phe Gly Gln Thr Gly Asp Thr Glu Ser
            20                  25                  30

Val Pro Asp Pro Gln Pro Ile Gly Glu Pro Pro Ala Ala Pro Ser Gly
        35                  40                  45

Val Gly Pro Thr Thr Met Ala Ser Gly
    50                  55

<210> SEQ ID NO 36
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Pro Gln Glu Pro Asp Ser Ser Ser Gly Ile Gly Lys Thr Gly Gln Gln
1               5                   10                  15

Pro Ala Lys Lys Arg Leu Asn Phe Gly Gln Thr Gly Asp Ser Glu Ser
            20                  25                  30
```

```
Val Pro Asp Pro Gln Pro Leu Gly Glu Pro Pro Ala Ala Pro Ser Gly
         35                  40                  45

Val Gly Ser Leu Thr Met Ala Ser Gly
     50                  55

<210> SEQ ID NO 37
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Pro Gln Glu Pro Asp Ser Ser Ala Gly Ile Gly Lys Ser Gly Ala Gln
1               5                   10                  15

Pro Ala Lys Lys Arg Leu Asn Phe Gly Gln Thr Gly Asp Ser Glu Ser
            20                  25                  30

Val Pro Asp Pro Gln Pro Leu Gly Glu Pro Pro Ala Thr Pro Ala Ala
         35                  40                  45

Val Gly Pro Thr Thr Met Ala Ser Gly
     50                  55

<210> SEQ ID NO 38
<211> LENGTH: 150
<212> TYPE: DNA
<213> ORGANISM: Adeno-associated virus

<400> SEQUENCE: 38
gccagcagcc cgctaaaaag agactcaatt ttggtcagac tggcgactca gagtcagtcc      60
ccgacccaca acctctcgga gaacctccag caaccccgc tgctgtggga cctactacaa     120
tggcttcagg cggtggcgca ccaatggcag                                      150

<210> SEQ ID NO 39
<211> LENGTH: 49
<212> TYPE: PRT
<213> ORGANISM: Adeno-associated virus
<220> FEATURE:
<221> NAME/KEY: MOD_RES
<222> LOCATION: (14)..(14)
<223> OTHER INFORMATION: Leu or Met

<400> SEQUENCE: 39

Gly Gln Gln Pro Ala Lys Lys Arg Leu Asn Phe Gly Gln Xaa Ala Thr
1               5                   10                  15

Gln Ser Gln Ser Pro Thr His Asn Leu Ser Glu Asn Leu Gln Gln Pro
            20                  25                  30

Pro Leu Leu Trp Asp Leu Leu Gln Trp Leu Gly Gly Gly Ala Pro Met
         35                  40                  45

Ala

<210> SEQ ID NO 40
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gtgcacagcc cgctaaaaag agactcaatt tcggtcagac tggcgacaca gagtcagtcc      60
```

```
cagaccctca accaatcgga gaacctcccg cagccccctc aggtgtggga tctcttacaa    120
tggcttcagg cggtggcgca ccaatggcag                                    150
```

```
<210> SEQ ID NO 41
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Leu or Met

<400> SEQUENCE: 41
```

Gly Ala Gln Pro Ala Lys Lys Arg Leu Asn Phe Gly Gln Xaa Ala Thr
1               5                   10                  15

Gln Ser Gln Ser Gln Thr Leu Asn Gln Ser Glu Asn Leu Pro Gln Pro
            20                  25                  30

Pro Gln Val Trp Asp Leu Leu Gln Trp Leu Gly Gly Gly Ala Pro Met
        35                  40                  45

Ala

```
<210> SEQ ID NO 42
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gccagcagcc cgctaaaaag agactcaatt ttggtcagac tggcgacaca gagtcagtcc    60
ccgacccaca acctatcgga gaacctccag cagccccctc aggtgtggga tctcttacaa    120
tggcttcagg cggtggcgca ccaatggcag                                    150
```

```
<210> SEQ ID NO 43
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Leu or Met

<400> SEQUENCE: 43
```

Gly Gln Gln Pro Ala Lys Lys Arg Leu Asn Phe Gly Gln Xaa Ala Thr
1               5                   10                  15

Gln Ser Gln Ser Pro Thr His Asn Leu Ser Glu Asn Leu Gln Gln Pro
            20                  25                  30

Pro Gln Val Trp Asp Leu Leu Gln Trp Leu Gly Gly Gly Ala Pro Met
        35                  40                  45

Ala

```
<210> SEQ ID NO 44
<211> LENGTH: 150
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 44
gccagcagcc cgctaaaaag agactcaatt ttggtcagac tggcgacaca gagtcagtcc    60
ccgacccaca acctatcgga gaacctccag cagccccctc aggtgtggga cctactacaa   120
tggcttcagg cggtggcgca ccaatggcag                                    150

<210> SEQ ID NO 45
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
gccagcagcc cgctaaaaag agactcaatt ttggtcagac tggcgactca gagtcagtcc    60
ccgacccaca acctctcgga gaacctccag cagccccctc aggtgtggga tctcttacaa   120
tggcttcagg cggtggcgca ccaatggcag                                    150

<210> SEQ ID NO 46
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gcgcgcagcc cgctaaaaag agactcaatt ttggtcagac tggcgactca gagtcagtcc    60
ccgacccaca acctctcgga gaacctccag caaccccgc tgctgtggga cctactacaa   120
tggcttcagg cggtggcgca ccaatggcag                                    150

<210> SEQ ID NO 47
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Leu or Met

<400> SEQUENCE: 47

Gly Ala Gln Pro Ala Lys Lys Arg Leu Asn Phe Gly Gln Xaa Ala Thr
1               5                   10                  15

Gln Ser Gln Ser Pro Thr His Asn Leu Ser Glu Asn Leu Gln Gln Pro
            20                  25                  30

Pro Leu Leu Trp Asp Leu Leu Gln Trp Leu Gly Gly Gly Ala Pro Met
        35                  40                  45

Ala

<210> SEQ ID NO 48
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Ala Thr Gln Ser Gln Ser Pro Thr Leu Asn Leu Ser Glu Asn Leu
1               5                   10                  15

Gln Gln Pro Pro Leu Val Trp Asp Leu Leu Gln Trp Leu Gln
            20                  25                  30

<210> SEQ ID NO 49
<211> LENGTH: 30
<212> TYPE: PRT
<213> ORGANISM: Adeno-associated virus

<400> SEQUENCE: 49

Met Ala Thr Gln Ser Gln Ser Pro Ile His Asn Leu Ser Glu Asn Leu
1               5                   10                  15

Gln Gln Pro Pro Leu Leu Trp Asp Leu Leu Gln Trp Leu Gln
            20                  25                  30

<210> SEQ ID NO 50
<211> LENGTH: 30
<212> TYPE: PRT
<213> ORGANISM: Adeno-associated virus

<400> SEQUENCE: 50

Met Glu Thr Gln Thr Gln Tyr Leu Thr Pro Ser Leu Ser Asp Ser His
1               5                   10                  15

Gln Gln Pro Pro Leu Val Trp Glu Leu Ile Arg Trp Leu Gln
            20                  25                  30

<210> SEQ ID NO 51
<211> LENGTH: 30
<212> TYPE: PRT
<213> ORGANISM: Adeno-associated virus

<400> SEQUENCE: 51

Met Ala Thr Gln Ser Gln Ser Gln Thr Leu Asn Leu Ser Glu Asn His
1               5                   10                  15

Gln Gln Pro Pro Gln Val Trp Asp Leu Ile Gln Trp Leu Gln
            20                  25                  30

<210> SEQ ID NO 52
<211> LENGTH: 24
<212> TYPE: PRT
<213> ORGANISM: Adeno-associated virus

<400> SEQUENCE: 52

Met Glu Gln Ala Thr Asp Pro Leu Arg Asp Gln Leu Pro Glu Pro Cys
1               5                   10                  15

Leu Met Thr Val Arg Cys Val Gln
            20

<210> SEQ ID NO 53
<211> LENGTH: 30
<212> TYPE: PRT
<213> ORGANISM: Adeno-associated virus

<400> SEQUENCE: 53

Met Ala Thr Gln Ser Gln Ser Pro Thr Leu Asn Leu Ser Glu Asn Leu
1               5                   10                  15

Gln Gln Arg Pro Leu Val Trp Asp Leu Val Gln Trp Leu Gln
            20                  25                  30

```
<210> SEQ ID NO 54
<211> LENGTH: 30
<212> TYPE: PRT
<213> ORGANISM: Adeno-associated virus

<400> SEQUENCE: 54

Met Ala Thr Gln Ser Gln Phe Gln Thr Leu Asn Leu Ser Glu Asn Leu
1               5                   10                  15

Gln Gln Arg Pro Leu Val Trp Asp Leu Ile Gln Trp Leu Gln
            20                  25                  30

<210> SEQ ID NO 55
<211> LENGTH: 30
<212> TYPE: PRT
<213> ORGANISM: Adeno-associated virus

<400> SEQUENCE: 55

Met Ala Ser Gln Ser Gln Ser Pro Thr Leu Asn Gln Ser Glu Asn His
1               5                   10                  15

Gln Gln Ala Pro Leu Val Trp Asp Leu Val Gln Trp Leu Gln
            20                  25                  30

<210> SEQ ID NO 56
<211> LENGTH: 24
<212> TYPE: PRT
<213> ORGANISM: Adeno-associated virus

<400> SEQUENCE: 56

Met Glu Pro Glu Thr Asp Pro Leu Lys Asp Gln Ile Pro Ala Pro Cys
1               5                   10                  15

Leu Gln Thr Leu Lys Cys Val Gln
            20
```